(12) United States Patent
Rubinstein et al.

(10) Patent No.: US 8,648,172 B2
(45) Date of Patent: Feb. 11, 2014

(54) ANTI-MUC1 α/β ANTIBODIES

(75) Inventors: Daniel B. Rubinstein, Silver Spring, MD (US); Daniel H. Wreschner, Efrat (IL)

(73) Assignees: Biomodifying, LLC, Silver Spring, MD (US); Ramot at Tel Aviv University Ltd., Tel Aviv (IL)

( * ) Notice: Subject to any disclaimer, the term of this patent is extended or adjusted under 35 U.S.C. 154(b) by 0 days.

(21) Appl. No.: 13/298,119

(22) Filed: Nov. 16, 2011

(65) Prior Publication Data

US 2012/0207772 A1 Aug. 16, 2012

Related U.S. Application Data

(63) Continuation of application No. 11/883,266, filed as application No. PCT/US2006/003213 on Jan. 27, 2006, now abandoned.

(60) Provisional application No. 60/647,870, filed on Jan. 28, 2005.

(51) Int. Cl.
*C07K 16/00* (2006.01)
*C12P 21/08* (2006.01)
*C07K 17/00* (2006.01)

(52) U.S. Cl.
USPC .............. 530/387.1; 530/387.3; 530/387.7; 530/388.1; 530/388.15; 530/388.8; 530/388.85; 530/391.1; 530/391.3; 530/391.7; 530/809

(58) Field of Classification Search
None
See application file for complete search history.

(56) References Cited

U.S. PATENT DOCUMENTS

| | | | |
|---|---|---|---|
| 5,530,101 | A | 6/1996 | Queen et al. |
| 6,716,966 | B1 | 4/2004 | Madiyalakan |
| 7,202,346 | B2 | 4/2007 | Payne et al. |
| 2002/0146750 | A1 | 10/2002 | Hoogenboom et al. |
| 2003/0235868 | A1 | 12/2003 | Hoogenboom et al. |
| 2004/0005647 | A1 | 1/2004 | Denardo et al. |
| 2004/0057952 | A1 | 3/2004 | Payne et al. |
| 2005/0019324 | A1 | 1/2005 | Wreschner et al. |
| 2005/0053606 | A1 | 3/2005 | Kufe et al. |

FOREIGN PATENT DOCUMENTS

| | | |
|---|---|---|
| WO | WO 96/03502 A2 | 2/1996 |
| WO | WO 00/52046 A1 | 9/2000 |
| WO | WO 01/70265 A2 | 9/2001 |
| WO | WO 02/078598 A2 | 10/2002 |
| WO | WO 02/079429 A2 | 10/2002 |
| WO | WO 03/031569 A2 | 4/2003 |
| WO | WO 03/088995 A2 | 10/2003 |
| WO | WO 2004/005470 A2 | 1/2004 |
| WO | WO 2007/039109 A1 | 4/2007 |

OTHER PUBLICATIONS

International Search Report from PCT/US2006/003213, dated Aug. 16, 2006.
Supplementary European Search Report from EP 06734050.5, mailed Apr. 14, 2009.
Denton, et al., "Production and Characterization of a Recombinant anti-MUC1 scFv Reactive with Human Carcinomas," British Journal of Cancer, vol. 76, No. 5, 1997, pp. 614-621.
Elamanchili et al., "Characterization of poly(D, L-lactic-co-glycolic-acid) based Nanoparticulate System for Enhanced Delivery of Antigens to Dendritic Cells," Vaccine, Butterworth Scientific., Guildford, GB, vol. 22, No. 19, (Jun. 23, 2004), pp. 2406-2412.
Hilkens, J. et al.; "Monoclonal antibodies against the nonmucin domain of JUC1/episialin". *Tumor Biology*; 1998; pp. 67-70; vol. 19, Suppl. 1.
Linsley, et al., "Monoclonal Antibodies Reactive with Mucin Glycoproteins Fuound in Sera From Breast Cancer Patients," Cancer Research, 48 (Apr. 15, 1988), pp. 2138-2148.
Nustad, K. et al.; "Specificity and affinity of 26 monoclonal antibodies against the CA 125 antigen: first report from the ISOBM TD-1 workshop"; *Tumor Biology*; 1996; pp. 196-219; vol. 17.
Price, M.R. et al.; "Summary Report on the ISOBM TD-4 Workshop: Analysis of 56 monoclonal antibodies against the MUC1 Mucin"; *Tumor Biology*; 1998; pp. 1-20.
Rubenstein et al., "MUC1/X Protein Immunization Enhances cDNA Immunization in Generating Anti-MUC1 α/β Junction Antibodies that Target Malignant Cells," Cancer Research, Dec. 1, 2006, vol. 66, No. 23, pp. 11247-11253.
Gendler et al.; "Molecular cloning and expression of human tumor-associated polymorphic epithelial mucin"; *J. Biol. Chem.*; 265(25):15286-15293 (1990).
Harlow, E. And D.P. Lane; "Antibodies: A Laboratory Manual"; Chapter 6: Monoclonal Antibodies, pp. 141-142; New York: Cold Springs Harbor (1988).
Janeway et al.; *Immunobioloqy*, $5_{th}$ Ed. (2001) New York: Garland Science . Terms *isotype* and *titer*. (www.garlandscience.com).
Levitin, Fiana, et al.; "The MUC1 SEA Module Is a Self-cleaving Domain"; *Journal of Biological Chemistry*; Sep. 30, 2005; pp. 33374-33386; vol. 280, No. 39.
Rubinstein et al.; "Immunization with MUC1/X Protein Enhances cDNA Immunization in Generating anti-MUC1 α/β Junction Antibodies that Target Cancer Cells"; *Clin. Cancer Res.*; vol. 11, No. 24 (Part 2 Suppl S), Abstract A61, p. 8980s (Nov. 14-18, 2005).
Wreschner et al.; "Human epithelial tumor antigen cDNA sequences : Differential splicing may generate multiple protein forms" *Eur. J. Biochem.*; 189(3): 463-473 (1990).

*Primary Examiner* — Peter J Reddig
(74) *Attorney, Agent, or Firm* — Kilpatrick Townsend & Stockton LLP

(57) ABSTRACT

The present invention provides antibodies that simultaneously bind the α- and β-subunits of an intact MUC1 protein, and methods for making and using such antibodies.

21 Claims, 8 Drawing Sheets

FIGURE 2

```
1    gaatc..................gaatctgttctgcccctcccacccatttcaccaccaccatg
     EcoRI                                    Signal peptide         1
61   acacgggcacccagtctcctttcttcctgctgctcctcacagtgcttacagttgtt
     T  P  G  T  Q  S  P  F  F │L  L  L  L  L  T  V  L  T  V  V│21
121  acaggttctggtcatgcaagctctaccccaggtggagaaaaggagacttcggctacccag
     T  G↑ S  G  H  A  S  S  T  P  G  G  E  K  E  T  S  A  T  Q  41
                                                    SPLICE
181  agaagttcagtgcccagctctactgagaagaatgct│gt│gagtatgaccagcagcgtactc
     R  S  S  V  P  S  S  T  E  K  N  A │V  S  M  T  S  S  V  L 61
241  tccagccacagcccggttcaggctcctccaccactcagggacaggatgtcactctggcc
     S  S  H  S  P  G  S  G  S  S  T  T  Q  G  Q  D  V  T  L  A 81
301  ccggccacggaaccagcttcaggttcagctgccacctggggacaggatgtcacctcggtc
     P  A  T  E  P  A  S  G  S  A  A  T  W  G  Q  D  V  T  S  V 101
361  ccagtcaccaggccagccctgggctccaccaccccgccagccacgatgtcacctcagcc
     P  V  T  R  P  A  L  G  S  T  T  P  P  A  H  D  V  T  S  A 121
421  ccggacaacaaggccgcccgggctccacgcccccacggtgtcacctcggcc
     P  D  N  K  P  A [P  G  S  T  A  P  P  A  H  G  V  T  S  A 141
481  ccggacaccaggccgcccgggctccacgcgcccgcagcccacggtgtcacctcggcc
     P  D  T  R  P  P [P  G  S  T  A  P  P  A  H  G  V  T  S  A 161
541  ccggacaccaggccgcccgggctccacgcgcccgcagcccacggtgtcacctcggcc
     P  D  T  R  P  P [P  G  S  T  A  P  A  A  H  G  V  T  S  A 181
601  ccggacaccaggccggcccgggctccacgcccccccagcccatggtgtcacctcggcc
     P  D  T  R  P  A  P  G  S  T  A  P  P  A  H  G  V  T  S  A 201
661  ccggacaacaggccgccttggcgtccacgcccctccagtccacaatgtcacctcggcc
     P  D  N  R  P  A  L  A  S  T  A  P  P  V  H  N  V  T  S  A 221
721  tcaggctctgcatcaggctcagcttctactctggtgcacaacggcacctctgcagggct
     S  G  S  A  S  G  S  A  S  T  L  V  H  N  G  T  S  A  R  A 241
781  accaacaccagccagcaagagcactccattctcaattcccagccaccactctgatact
     T  T  T  P  A  S  K  S  T  P  F  S  I  P  S  H  H  S  D  T 261
841  cctaccacccttgccagccatagcaccaagactgatgccagtagcactcaccatagcacg
     P  T  T  L  A  S  H  S  T  K  T  D  A  S  S  T  H  H  S  T 281

Splice Acceptor [MUC1/X]
901  gtacctcctctcacctcctccaatcacagcacttctccccag│tgtctactggggtctct
     V  P  P  L  T  S  S  N  H  S  T  S  P  Q │L  S  T  G  V  S 301

Splice Acceptor [MUC1/Y]
961  ttcttttcctgtcttttcacatttcaaacctccag│ttaattcctctctggaagatccc
     F  F  F  L  S  F  H  I  S  N  L  Q │F  N  S  S  L  E  D  P 321
1021 agcaccgactactaccaagagctgcagagagacatttctgaaatgttttttgcagatttat
     S  T  D  Y  Y  Q  E  L  Q  R  D  I  S  E  M  F  L  Q  I  Y 341
```

FIGURE 2- Continued

```
1081 aaacaaggggg ttttctgggcctctccaatattaagttcaggccaggatctgtggtggta
      K  Q  G  G  F  L  G  L  S  N  I  K  F  R  P  G  S  V  V  V  361
1141 caattgactctggccttccgagaaggtaccatcaatgtccacgacgtggagacacagttc
      Q  L  T  L  A  F  R  E  G  T  I  N  V  H  D  V  E  T  Q  F  381
1201 aatcagtataaaacggaagcagcctctcgatataacctgacgatctcagacgtcagcgtg
      N  Q  Y  K  T  E  A  A  S  R  Y  N  L  T  I  S  D  V  S  V  401
1261 agtgatgtgccatttcctttctctgcccagtctggggctgggtgccaggctggggcatc
      S  D  V  P  F  P  F  S  A  Q  S  G  A  G  V  P  G  W  G  I  421
1321 gcgctgctggtgctggtctgtgttctggttgcgctggccattgtctatctcattgccttg
      A  L  L  V  L  V  C  V  L  V  A  L  A  I  V  Y  L  I  A  L  441
1381 gctgtctgtcagtgccgccgaaagaactacgggcagctggacatctttccagcccgggat
      A  V  C  Q  C  R  R  K  N  Y  G  Q  L  D  I  F  P  A  R  D  461
1441 acctaccatcctatgagcgagtaccccacctaccacacccatgggcgctatgtgccccct
      T  Y  H  P  M  S  E  Y  P  T  Y  H  T  H  G  R  Y  V  P  P  481
1501 agcagtaccgatcgtagcccctatgagaaggtttctgcaggtaatggtggcagcagctc
      S  S  T  D  R  S  P  Y  E  K  V  S  A  G  N  G  G  S  S  L  501
1561 tcttacacaaacccagcagtggcagccacttctgccaacttgtaggggcacgtcgccctc
      S  Y  T  N  P  A  V  A  A  T  S  A  N  L  -              515
1621 tgagctgagtggccagccagtgccattccactccactcagggctctctgggccagtcctc
1681 ctgggagccccaccacaacacttccaggcatggaattcc
```

ANTI-MUC1 α/β ANTIBODIES

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED AS AN ASCII TEXT FILE

The Sequence Listing written in file -1-2.TXT, created on Jan. 27, 2012, 24,576 bytes, machine format IBM-PC, MS-Windows operating system, is hereby incorporated by reference in its entirety for all purposes.

FIELD OF THE INVENTION

The invention relates to antibodies that specifically and concurrently bind to both the α-subunit and the β-subunit of MUC1.

BACKGROUND OF THE INVENTION

MUC1 is a glycoprotein highly expressed in a number of human epithelial malignancies, including breast, prostate, colon, ovarian and pancreatic carcinomas, as well as on the malignant plasma cells of multiple myeloma. Although alternative splicing can generate a variety of MUC1 isoforms, the most intensively studied MUC1 protein is a type I transmembrane protein comprised of a heavily glycosylated extracellular domain containing a tandem-repeat-array, a transmembrane domain, and a cytoplasmic domain (MUC1/TM). MUC1/TM is proteolytically cleaved soon after its synthesis generating two subunits, α and β which specifically recognize and bind in a strong non-covalent interaction (see, FIG. 1, MUC1/TM). Cleavage of MUC1 into the two subunits occurs in the SEA module, a highly-conserved domain found in a number of cell-tethered mucin-like proteins (Levitin, et al., *J Biol Chem* (2005) 280:33374-86). Shedding of the α-subunit from the cell membrane results in soluble tandem-repeat-array-containing MUC1 in the peripheral circulation, and it is this molecule which is used to determine serum MUC1 levels in patients with MUC1 positive malignancies.

The presence of the soluble α-subunit MUC1 protein in the circulation presents a singular difficulty in delivering adequate amounts of anti-MUC1 antibodies to directly target MUC1-expressing malignant cells. This is because the most immunogenic part of MUC1 is the tandem-repeat-array and almost all anti-MUC1 antibodies generated to date exclusively recognize epitopes in that immunogenic region. Sequestration of anti-tandem repeat antibodies by the soluble, circulating MUC1 α-subunit severely limits the amount of antibody which can successfully bind MUC1 on the cell surface. Furthermore, deposition of immune complexes of anti-tandem repeat antibodies and its soluble, circulating MUC1 target can lead to significant end-organ damage.

In recent years, numerous efforts have been made to generate effective anti-MUC1 antibodies using the full-length MUC1/TM molecule as immunogen. The major obstacle hampering those attempts is that immunization with the whole MUC1/TM molecule invariably results in an antibody response composed almost in its entirety of antibodies recognizing epitopes on the highly immunogenic tandem repeat array. For ultimate application in in vivo targeting of MUC1-expressing tumor cells, such antibodies pose all the shortcomings inherent in anti-repeat antibodies, as detailed above.

Antibodies recognizing MUC1 epitopes tethered to the cell surface potentially obviate these difficulties. Although conceptually simple, generation of monoclonal antibodies to MUC1 stably tethered to the cell surface first requires characterization of cell-bound, non-shedding epitopes. The junction formed by the MUC1 α-subunit binding the membrane-tethered β-subunit provides such an epitope.

BRIEF SUMMARY OF THE INVENTION

The present invention provides antibodies that concurrently bind to both the α-subunit and the β-subunit of an intact MUC1 protein ("anti-MUC1 α/β antibodies" which bind to the MUC1 α/β subunit junction but does not substantially bind to either the MUC1 α-subunit or the MUC1 β-subunit in the absence of the other). The invention further provides methods for producing such antibodies and for using the antibodies, for example, in diagnostic and immunotherapeutic applications.

Accordingly, in a first aspect, the invention provides MUC1-specific antibodies that bind to the intact MUC1 protein with the proviso that the antibody does not bind to either the α-subunit or the β-subunit in the absence of the other.

With regard to embodiments of the antibodies, in some embodiments, the antibody binds to isoform MUC1/X but does not bind to isoform MUC1/Y, for example, as measured in an ELISA or by flow cytometry using cells expressing a MUC1 isoform. In some embodiments, the antibody binds to a MUC1/X isoform that is cleaved into a truncated α-subunit and a β-subunit.

The antibody can be polyclonal or monoclonal. The antibody can have a dissociation constant (Kd) in the range from about $10^{-7}$M to about $10^{-12}$M, for example about $10^{-7}$M, $10^{-8}$M, $10^{-9}$M, $10^{-10}$M, $10^{-11}$M, $10^{-12}$M. The antibody can have an association constant (Ka) in the range from about $10^6 M^{-1}$ to about $10^{10} M^{-1}$, for example, about $10^6$, $10^7$, $10^8$, $10^9$ $M^{-1}$, or $10^{10}$ $M^{-1}$. The antibody can have a titer of from about 1:100 or 1:300 to about 1:30,000 or 1:50,000, for example, about 1:300, 1:1000, 1:5000, 1:10,000, 1:20,000, 1:30,000, 1:50,000, as measured in an ELISA assay, using MUC1/TM or MUC1/X as an antigen.

The antibody can comprise any naturally occurring constant region or any of their subclasses, including, for example, IgA (including IgA1 and IgA2), IgD, IgE, IgG (including IgG1, IgG2, IgG3, and IgG4), and IgM. The antibodies can have a constant region from any animal able to produce antibodies, including mammal or avian. The antibodies can be produced in humans and non-human mammals, including canine, feline, bovine, ovine, equine, porcine and rodentia, including lagomorpha, rattus, hamster, murine. The antibodies can be produced in chickens.

In some embodiments, the antibodies are humanized or are human. In some embodiments, the antibodies lack a constant region. For example, the antibodies can be Fab fragments or single chain variable regions. The antibodies can be recombinantly produced.

The antibodies can further comprise a cytotoxic moiety, for example, a ricin molecule, a pseudomonas toxin, a radioisotope. The antibodies can further comprise a label moiety, for example, a radioisotope, an enzyme, a fluorophore.

In some embodiments, the antibodies prevent the dissociation of a MUC1 α-subunit from the β-subunit. In some embodiments, the antibodies decrease or inhibit intracellular signaling through a MUC1 β-subunit.

In some embodiments, the antibody is DMC209 or DMC111.

The invention further provides for cells comprising anti-MUC1 α/β antibodies. For example, the cell can be a hybridoma that produces the antibody. The cell also can be a cell with an intact MUC1 protein on its surface, wherein the MUC1 protein is bound (i.e., attached) to an anti-MUC1 α/β antibody. The cell can also be recombinantly modified to express an antibody of the invention.

In another aspect, the invention provides for methods of targeting an immunotoxin to a MUC1 overexpressing cancer cell and methods of inhibiting or preventing the growth of a MUC1 overexpressing cancer cell by administering a therapeutically sufficient amount of an anti MUC1 α/β antibody of the invention.

In a further aspect, the invention provides a method of producing a MUC1-specific antibody that binds to the intact MUC1 protein, comprising the steps of:
 i) immunizing a subject having the ability to produce antibodies one or more times with a MUC1/TM antigen including the α subunit tandem repeats in an amount sufficient to yield a MUC1-specific antibody that binds to the intact MUC1 protein; and
 ii) selecting for antibodies that bind to a MUC1/X antigen; wherein the antibody does not bind to either the MUC1 α-subunit or the MUC1 β-subunit in the absence of the other.

In a further embodiment of the methods, the subject can be immunized one or more times with an isoform MUC1/X antigen subsequent to immunization with a MUC1/TM antigen. Immunization with a MUC1 antigen can optionally include an adjuvant.

The MUC1/TM and MUC1/X antigens independently can be administered to the subject in the form of a nucleic acid or a polypeptide. In one embodiment, the subject is first immunized one or more times with a nucleic acid (e.g., cDNA) encoding a MUC1/TM antigen and then subsequently immunized one or more times with a nucleic acid encoding a MUC1/X antigen.

In another aspect, the invention provides for a method of screening for a MUC1-specific antibody that binds to the intact MUC1 protein with the proviso that the antibody does not bind to either the α-subunit or the β-subunit in the absence of the other, comprising
 i) determining the binding of a plurality of anti-MUC1 generated antibodies to a cleaved MUC1/X antigen and a MUC1/Y antigen; and
 ii) selecting for antibodies that specifically bind to the MUC1/X antigen but do not significantly bind to the MUC1/Y antigen.

The embodiments of the antibodies produced or used in the methods are the same as described above.

In a related aspect, the invention provides a method of producing an antibody against an antigen of interest, comprising the steps of:
 i) immunizing a subject one or more times with a MUC1/TM antigen including the α subunit tandem repeats and the antigen of interest; and
 ii) immunizing the subject one or more times with the antigen of interest;
whereby antibodies against the antigen of interest are produced.

The MUC1/TM antigen and the antigen of interest independently can be administered to the subject in the form of a nucleic acid or a polypeptide.

In some embodiments, the MUC1/TM antigen and the antigen of interest are administered together. In some embodiments, the MUC1/TM antigen and the antigen of interest are joined by a chemical linker. In some embodiments, the MUC1/TM antigen and the antigen of interest are administered as a fusion protein.

The antigen of interest can be any antigenic polypeptide sequence or any nucleic acid encoding an antigenic polypeptide sequence. An antigen of interest can be without limitation human, mammalian, animal, plant, bacterial, viral or synthetic. An antigen of interest can be a tumor-associated antigen (e.g., carcinoembryonic antigen (CEA), carbohydrate antigen (CA-125), prostate stem cell antigen (PSCA), melanoma antigens (MAGE, MART). An antigen of interest can be an infectious disease associated antigen.

DEFINITIONS

Unless defined otherwise herein, all technical and scientific terms used herein have the same meaning as commonly understood by one of ordinary skill in the art to which this invention belongs. For example, the *Concise Dictionary of Biomedicine and Molecular Biology*, Juo, Pei-Show, 2nd ed., 2002, CRC Press; *The Dictionary of Cell and Molecular Biology*, 3rd ed., 1999, Academic Press; and the *Oxford Dictionary Of Biochemistry And Molecular Biology*, Revised, 2000, Oxford University Press provide one of skill with a general dictionary of many of the terms used in this invention.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. For purposes of the present invention, the following terms are defined below.

The terms "bind(s) specifically" or "specifically bind(s)" or "attached" or "attaching" refers to the preferential association of an anti-MUC1 α/β antibody, in whole or part, with a cell or tissue bearing a particular target epitope (i.e., a MUC1 α/β junction) in comparison to cells or tissues lacking that target epitope. It is, of course, recognized that a certain degree of non-specific interaction may occur between an antibody and a non-target epitope. Nevertheless, specific binding, may be distinguished as mediated through specific recognition of the target epitope. Typically specific binding results in a much stronger association between the delivered molecule and an entity (e.g., an assay well or a cell) bearing the target epitope than between the bound antibody and an entity (e.g., an assay well or a cell) lacking the target epitope. Specific binding typically results in greater than about 10-fold and most preferably greater than 100-fold increase in amount of bound anti-MUC1 α/β antibody (per unit time) to a cell or tissue bearing the target epitope as compared to a cell or tissue lacking the target epitope. Specific binding between two entities generally means an affinity of at least $10^6$ $M^{-1}$. Affinities greater than $10^8$ $M^{-1}$ are preferred. Specific binding can be determined using any assay for antibody binding known in the art, including Western Blot, ELISA, flow cytometry, immunohistochemistry.

The phrase "not substantially bind" is meant that no more than about 10-15% of an anti-MUC1 α/β antibody which specifically binds to a target epitope is bound to a particular non-target epitope. "Not substantially binding" of an antibody to an entity lacking the target epitope will be about 10-fold less, and preferably about 100-fold less, than specific binding of the antibody to the same entity bearing the target epitope.

The term "MUC1" or "mucin 1" refers to polymorphic variants, alleles, mutants, and interspecies homologs that: (1)

have about 85%, 90%, 95%, 96%, 97%, 98%, 99% amino acid sequence identity to a native MUC1 protein, including for example, GenBank Accession Nos. NP_002447 (MUC1 mucin isoform 1), NP_001018016 (MUC1 mucin isoform 2), NP_001018017 (MUC1 mucin isoform 3), or NP_001018021 (MUC1 mucin isoform 4), isoform MUC1/TM, isoform MUC1/X, isoform MUC1/Y over a window of about 25 amino acids, optionally 50, 100, 150, 200, 250 amino acids; (2) specifically bind to antibodies raised against an immunogen comprising an amino acid sequence of a native MUC1 protein (including glycosylated amino acid sequences), and conservatively modified variants thereof; or (3) have about 85%, 90%, 95%, 96%, 97%, 98%, 99% nucleic acid sequence identity to a native MUC1 nucleic acid sequence, including for example, GenBank Accession Nos. NM_002456 (MUC1 transcript variant 1), NM_001018016 (MUC1 transcript variant 2), NM_001018017 (MUC1 transcript variant 3), or NM_001018021 (MUC1 transcript variant 4), variant MUC1/TM, variant MUC1/X, variant MUC1/Y over a window of about 25 nucleic acids, optionally 50, 100, 150, 200, 250, 500 nucleic acids.

MUC1 is a cell surface and/or serum tumor marker glycoprotein characterized by repeat domains and dense O-glycosylation (Baldus, et al., *Crit Rev Clin Lab Sci* (2004) 41:189; Karsten, et al., (2005) 26:217). MUC1 is expressed at the luminal surface of most simple epithelial cells, and is overexpressed on carcinoma cells of a number of epithelial malignancies, including breast, prostate, ovarian and pancreatic carcinomas, and malignant plasma cells (e.g., multiple myeloma) (See, Taylor-Papadimitriou, et al., *J Mammary Gland Biol Neoplasia* (2002) 7:209; Denda-Nagai and Irimura, *Glycoconj J* (2000) 17:649). MUC1 is comprised of a soluble α-subunit and a cell-anchored β-subunit. MUC1 binds to intercellular adhesion molecule-1 (ICAM-1), mediating cell-cell adhesion (Baldus, et al., supra and Rahn, et al., *J Biol Chem* (2004) 279:29386) and functions as a docking protein for signaling molecules. MUC1 has a highly conserved cytoplasmic tail, which binds transcription regulator beta-catenin in a process that is tightly regulated by MUC1 phosphorylation (see, Carraway, et al., *Bioessays* (2003) 25:66).

The term "intact MUC1 protein" as used herein refers to a MUC1 protein that has been cleaved into an α-subunit and a β-subunit, and each subunit has native tridimensional folding and the subunits are interacting with each other. MUC1 isoforms MUC1/TM and MUC1/X can be an intact MUC1 protein.

A "MUC1/X" isoform lacks an antigenic tandem-repeat-array in the α-subunit, and is cleaved within the SEA module into a truncated α-subunit and a β-subunit (see, Levitin, et al. supra).

A "MUC1/Y" isoform lacks an antigenic tandem-repeat-array in the α-subunit, and is not cleaved within the SEA module (see, Levitin, et al. supra).

The term "physiological conditions" refers to an extracellular milieu having conditions (e.g., temperature, pH, and osmolarity) which allows for the sustenance or growth of a cell of interest.

The term "antibody" refers to an immunoglobulin molecule obtained by in vitro or in vivo generation of the humoral response, and includes both polyclonal and monoclonal antibodies. The term also includes genetically engineered forms such as chimeric antibodies (e.g., humanized murine antibodies), heteroconjugate antibodies (e.g., bispecific antibodies), and recombinant single chain Fv fragments (scFv). The term "antibody" also includes antigen binding forms of antibody fragments (e.g., Fab, F(ab)$_2$, $V_H$-$V_L$ Fab fragments).

The term "humanized antibody" refers to an antibody which comprises a non-human amino acid sequence but whose constant region has been altered to reduce immunogenicity in humans.

The term "human antibody" refers to an antibody produced by human immunoglobulin genes. A human antibody can be produced in vivo, for example, in a human, by a non-human animal (for example a mouse, a hamster, a rabbit, a cow) having functional human immunoglobulin genes. Such transgenic animals are known in the art. See, for example, Lonberg, *Nat Biotech* (2005) 23:1117; Robl, et al., *Theriogenology*, (2003) 59:107; and Ishida, et al., *Cloning Stem Cells* (2002) 4:91. Companies producing fully human antibodies from transgenic mice include Medarex, Milpitas, Calif. and Abgenix (now Amgen), Fremont, Calif. A human antibody can be produced in vitro, for example, from a combinatorial library of human immunoglobulin genes.

The term "extracellular" refers to the region extending outward from the lipid bilayer encompassing a cell.

The term "antigen" refers to any molecule that can bind specifically to an antibody. Antigens that can induce antibody production are called "immunogens." See, Janeway, et al., *Immunobiology*, 5th Edition, 2001, Garland Publishing. For the purposes of the present invention, an antigen can be a polypeptide or a nucleic acid (e.g., cDNA) that encodes an antigenic polypeptide.

The term "epitope" or "antigenic determinant" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding (i.e., conformationally determined) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, Glenn E. Morris, Ed. (1996). Antibodies that recognize the same epitope can be identified in a simple immunoassay showing the ability of one antibody to block the binding of another antibody to a target antigen (e.g., a competitive ELISA or solid phase radioimmunoassay (SPRIA)). T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., *J. Inf. Dis.* 170, 1110-19 (1994)), by antigen-dependent killing (cytotoxic T lymphocyte assay, Tigges et al., *J. Immunol.* (1996) 156:3901-3910) or by cytokine secretion.

BRIEF DESCRIPTION OF THE DRAWINGS

FIG. 2 illustrates the sequences of MUC1/TM, MUC1/X and MUC1/Y isoforms. MUC1/TM nucleotide (SEQ ID NO:7) and amino acid (SEQ ID NO:2) numbering are presented at left and right of sequence, respectively. Signal peptide cleavage occurs between glycine 23 and serine 24 and is indicated by the upward-facing arrow. The N30 sequence spans from SGHAS (SEQ ID NO:9) to EKNA (SEQ ID NO:10). For clarity, the spliced out central region comprising the tandem repeat array and its flanking sequences has been deleted and is indicated by the dashed line. Cleavage of MUC1/TM occurs between glycine 357 and serine 358 (between MUC1/X amino acid numbers 62 and 63) and is indicated by the upward-facing arrow. The splice donor site generating MUC1/X and MUC1/Y is shown at nucleotide 217 (gtgag), and splice acceptor sites generating MUC1/X and MUC1/Y are at nucleotides 942 (ccccag) and 996 (ctccag), respectively. The MUC1/X amino acids immediately C-terminal to the MUC1/X splice acceptor site are numbered in italics from 1 (initiating with LSTG; SEQ ID NO:12) to 120 (SGAG; SEQ ID NO:13), which is immediately N-terminal to the transmembrane domain (SEQ ID NO:11). The MUC1/X nucleic acid and amino acid sequences are presented as SEQ ID NOS:3 and 4, respectively. The MUC1/Y nucleic acid and amino acid sequences are presented as SEQ ID NOS:5 and 6, respectively. See, Levitin, et al., supra.

DETAILED DESCRIPTION

Introduction

Figure 1:
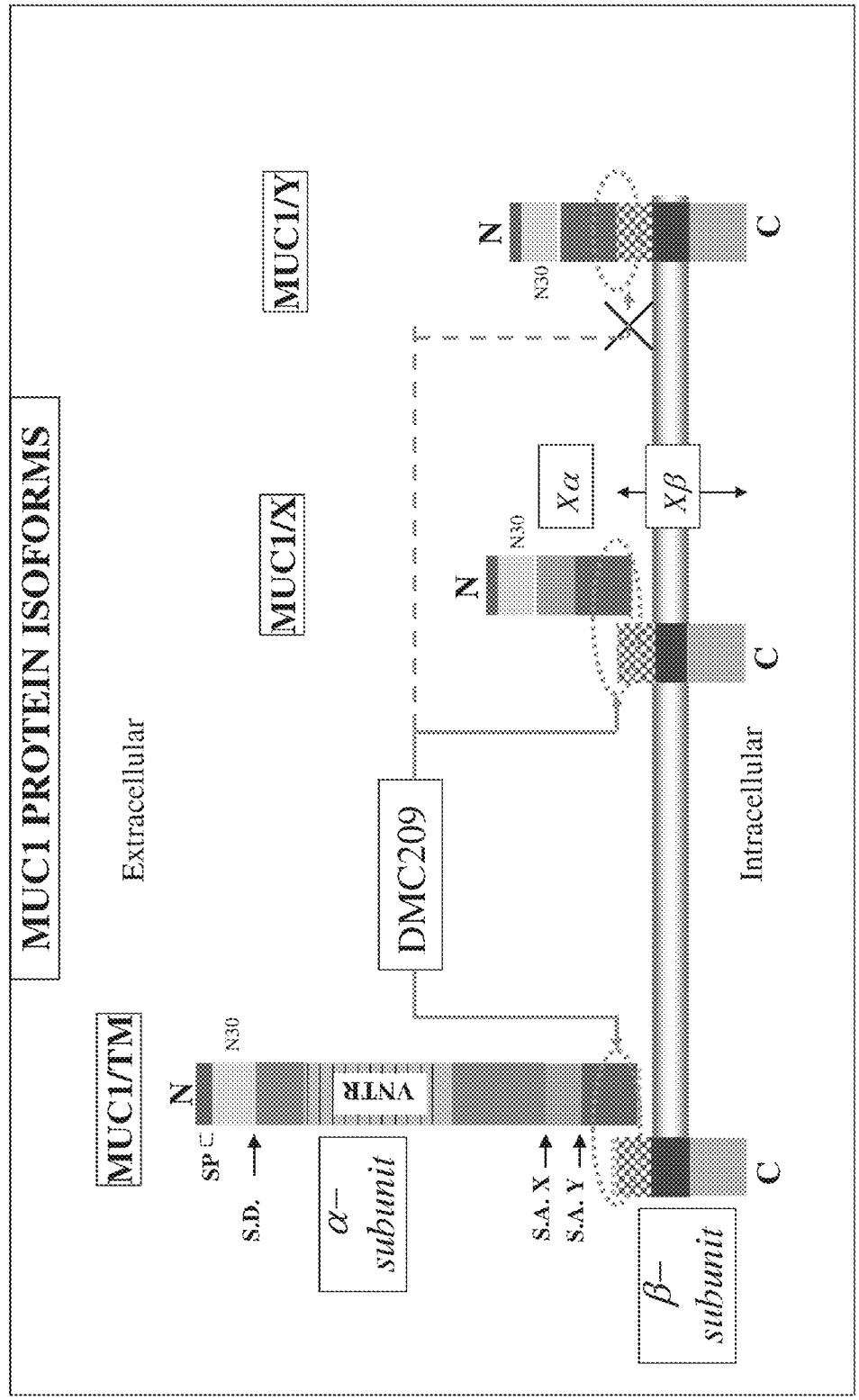
FIG. 1 illustrates MUC1 protein isoforms and MUC1 fusion proteins. The cleaved transmembrane MUC1 protein containing the tandem repeat array (MUC1/TM) is depicted at left. Alternative splicing utilizes a splice donor indicated by S.D.→resulting in one of two alternative splice acceptors (S.A. Y→ and S.A. X→) that form the MUC1/Y and MUC1/X isoforms. As described in the text, antibody DMC209 recognizes the cleaved α/β junction present in both the MUC1/X and MUC1/TM proteins, but does not react with the uncleaved MUC1/Y protein.
Figure 3:
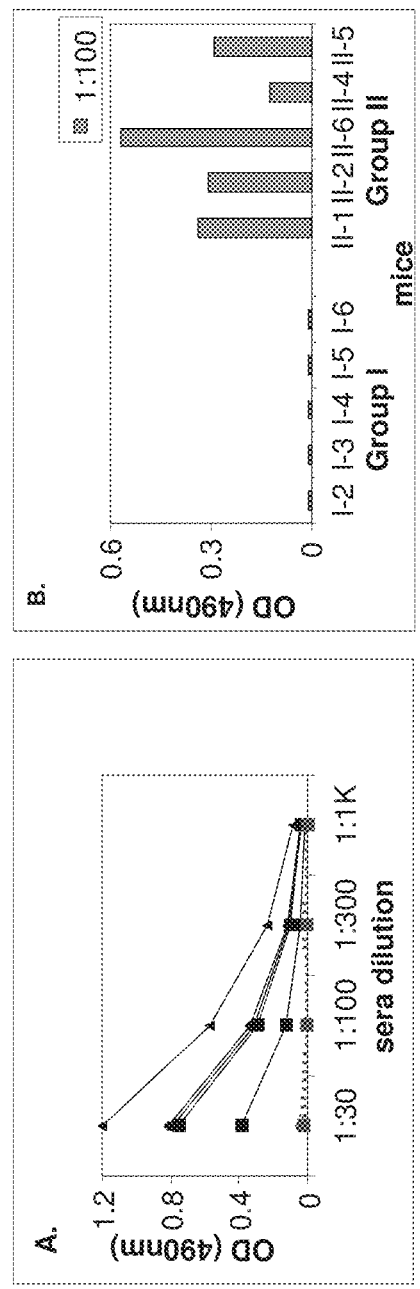
FIGS. 3A and B illustrate anti-MUC1/X antibodies generated in mice immunized with DNA coding for either MUC1/TM or MUC1/X. Mice were immunized with expression vectors containing cDNA coding for either the MUC1/TM protein (Group II) or with cDNA coding for MUC1/X protein from which the tandem repeat is deleted (Group I, see FIG. 1). Sera were assayed for antibody titers directed against the cleaved MUC1/X protein as described in the Examples. All Group II mice demonstrated significant anti-MUC1/X antibody titers whereas no anti-MUC1/X antibodies were detected in Group I mice (A and B).

We investigated the mechanism whereby the cleaved junction composed of the MUC1 α-subunit and β-subunit is formed. In the course of those studies, we analyzed the 'cleavageability' of the MUC1/TM, MUC1/Y and MUC1/X proteins (FIG. 1 and Levitin, et al., *J Biol Chem*, (2005) 280: 33374, hereby incorporated herein by reference in its entirety for all purposes). The MUC1/Y and MUC1/X isoforms are generated from mRNAs spliced at two distinct sites that utilize donor and acceptor sites located upstream and downstream to the tandem-repeat-array, and as a result in both isoforms the tandem-repeat-array and flanking sequences are spliced out (FIG. 1 and Levitin, et al.). The extracellular domains both of MUC1/X and MUC1/Y are thus considerably less complex than the large tandem-repeat-array-containing MUC1/TM protein. In fact, in its extracellular domain the MUC1/X protein comprises only the 120-amino acid SEA module fused to the MUC1 30 N-terminal amino acids. MUC1/Y is identical to MUC1/X except for an 18-amino acid deletion at the SEA module N terminus. Significantly, the MUC1/X isoform is cleaved at an identical site as the full-length MUC1/TM protein and thereby results in the same non-covalent interaction of the α-subunit and β-subunit. In contrast, the SEA module N-terminal truncation present in the MUC1/Y isoform results in a non-cleaved protein.

In order to generate antibodies directly targeting cancer cells, we surmised that antibodies specific for the MUC1 α/β junction ("anti-MUC1 α/β antibodies (Abs)") would target only membrane-bound MUC1. To circumvent generation of anti-tandem-repeat-array antibodies, we made use of the cleaved MUC1/X protein both as immunogen and as screening reagent. We report here a novel procedure in which mice were initially primed with MUC1/TM (e.g., DNA) to elicit an anti-MUC1/TM response. The resultant immune response contains antibodies reactive with the MUC1/X isoform. To further increase anti-MUC1/X titers, mice were boosted with MUC1/X (e.g., soluble protein). This resulted in exceptionally high anti-MUC1/X titers. Using this protocol we were successful in generating monoclonal antibodies which not only recognize cleaved MUC1 α/β junction on the cell surface, but also bind malignant cells expressing the full-length MUC1/TM.

Accordingly, the present invention provides antibodies that bind to the MUC1 α/β junction of an intact MUC1 protein on a cell, herein referred to as "anti-MUC1 α/β Abs." The antibodies simultaneously bind a conformationally determined epitope comprised of both the α-subunit and the β-subunit of an intact MUC 1 protein. The invention is based, in part, on the surprising discovery that the MUC1 isoform MUC1/X, which has no immunogenic tandem repeat region, is immunogenic and can be cleaved analogously to the full-length MUC1 isoform MUC1/TM (see, Levitin, et al., supra).
Antibodies Antigens and Immunization The anti-MUC1 α/β antibodies of the present invention are directed against the α/β junction of an intact MUC1 protein. They are produced by first immunizing a subject able to produce antibodies one or more times with a MUC1 α/β-subunit sequence (e.g., nucleic acid or soluble protein) that comprises an immunogenic tandem repeat sequence ("VNTR") (see, FIG. 1 and Gendler, et al., *J Biol Chem* (1990) 265:15286; Ligtenberg, et al., *J Biol Chem* (1990) 265:5573; and Wreschner, et al., *Eur J Biochem* (1990) 189: 463), for example, MUC1/TM. Optionally, the subject can be boosted with one or more subsequent immunizations against a truncated MUC1 α/β-subunit sequence (e.g., nucleic acid or soluble protein), lacking an immunogenic tandem repeat sequence, but retaining a viable cleavage sequence segment for cleavage into the α- and β-subunits, for example, isoform MUC1/X. See, FIG. 1 and Levitin, et al., *J Biol Chem* (2005) 280:33374, hereby incorporated herein by reference in its entirety for all purposes.

The antigens are generally prepared as soluble MUC1 polypeptides (i.e., that lack a transmembrane sequence) or nucleic acids that encode MUC1 polypeptide sequences (with or without a transmembrane sequence). The antigens, DNA or protein, can be isolated or purified from cells expressing or over-expressing MUC1, or from cells modified to recombinantly express MUC1 antigens, for example, bacterial, yeast or mammalian cell expression systems well known in the art. Recombinantly expressed MUC1 antigens can conveniently have optionally removable purification and/or detection tags, including without limitation, FLAG (DYKDDDDK; SEQ ID NO:15), sequential histidines, immunoglobulin constant regions (Fc), etc. See, Levitin, et al., supra.

In one embodiment, anti-MUC1 α/β antibodies can be produced by one or more primary immunizations with MUC1/TM cDNA and one or more secondary or booster immunizations with a MUC1/X cDNA. In one embodiment, anti-MUC1 α/β antibodies can be produced by one or more primary immunizations with MUC1/TM cDNA and one or more secondary or booster immunizations with a soluble MUC1/X protein.

Repeated immunizations are usually given to a subject at intervals of at least 2, 3, 4, 5, 6, 7, 8 weeks, or 3, 4, 5, 6 months, as appropriate. Repeated immunization can be administered at regularly spaced intervals, but need not be. Subjects receiving repeated immunizations can be administered the primary antigen (e.g. MUC1/TM) and/or the secondary antigen (e.g., MUC1/X) 1, 2, 3, 4, 5 or more times, as needed.

The anti-MUC1 α/β antibodies are identified by selecting for those that simultaneously bind to the MUC1 α- and β-subunits of a MUC1/X isoform, preferably a cleaved MUC1/X isoform. Preferred antibodies do not bind to the uncleavable MUC1/Y isoform or to either the α-subunit or β-subunit alone.

Production of Antibodies

Anti-MUC1 α/β antibodies can be polyclonal, monoclonal, Fab fragments (lacking a constant Fc region) or recombinant single chain Fv antibodies. Methods of producing polyclonal and monoclonal antibodies are known to those of skill in the art. See, e.g., Coligan, et al., *Current Protocols in Immunology*, 1991-2006, John Wiley & Sons; and Harlow and Lane (1989) *Antibodies: A Laboratory Manual*, Cold Spring Harbor Press, N.Y.; Harlow and Lane (1998) *Using Antibodies: A Laboratory Manual*, Cold Spring Harbor Press, N.Y.; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256: 495-497; See, Huse et al. (1989) *Science* 246: 1275-1281; and Ward, et al. (1989) *Nature* 341: 544-546. Birch and Lennox, *Monoclonal Antibodies: Principles and Applications*, Wiley-Liss, New York, N.Y. (1995). Anti-MUC1 α/β antibodies and B cells producing anti-MUC1 α/β antibodies can be elicited in any convenient animal capable of producing antibodies, for example, mammal or avian. For example, anti-MUC1 α/β antibodies conveniently can be produced in sheep or goats (ovine), or rodents (lagomorpha, rattus, hamster, murine), or chickens (gallus).

Other suitable techniques for antibody preparation include selection of libraries of recombinant immunoglobulin genes, including human immunoglobulin genes, in phage vectors and other vectors, including viral, bacterial and yeast vectors. High affinity antibodies to the MUC1 α/β junction can be rapidly isolated by using vector display (e.g., phage) methods to express, for example, recombinant single chain Fv (scFv) fragments or $V_H$-$V_L$ Fab fragments on the vector surface. Briefly, genes encoding the surface protein of a vector are altered so as to allow the insertion of an antibody gene which is expressed as a fusion protein on the surface of the vector that carries the gene. The vector expressing the desired antibody can be selectively enriched and isolated by virtue of its affinity/avidity for a junction of the MUC1 α/β subunits. The DNA encoding the antibody is packaged in the same vector and which allows the gene encoding the antibody to be isolated. A variety of such methods are amply discussed in the literature and well known to the skilled artisan. See, e.g., Winter et al., *Annu. Rev. Immunol.* 12:433-455 (1994); Marks et al., *J. Mol. Biol.* 222:581-597 (1991); Vaughan et al., *Nature Biotechnology* 14:309-314 (1996), Hallborn and Carlsson, *Biotechniques*, (2002) Suppl: 30-7, U.S. Pat. Nos. 4,642,334; 4,816,397; 4,816,567; 4,704,692; WO 86/01533; WO 88/09344; WO 89/00999; WO 90/02809; WO 90/04036; EP 0 324 162; and EP 0 239 400.

Preferably, antibodies will be constructed to minimize immunogenicity in the host as, for example, by maximizing the number of autologous (self) sequences present in the antibody. Accordingly, chimeric antibodies having non-xenogenic variable regions are preferred. Particularly preferred are the use of antibodies in which xenogenic portions are excluded, or are essentially limited to the complementarity determining regions (i.e., "humanized antibodies").

Antibody Binding Assays

Antibody binding to an intact MUC1 protein can be determined using techniques well known in the art, for example, an ELISA assay, a flow cytometry assay or a immunohistochemistry assay. In carrying out the binding assays, a test assay can be compared to a positive control and/or a negative control.

ELISA

With regard to an ELISA assay, ELISA plates can be coated with a soluble MUC1 α/β subunit protein antigen lacking the immunogenic tandem repeat region (e.g., isoform MUC1/X or MUC1/Y, lacking a transmembrane region). Preferably, the truncated MUC1 α/β subunit protein antigen can be cleaved into a truncated α-subunit and the extracellular region of a β-subunit (e.g., isoform MUC1/X). The coating protein antigen can be cleaved into an α-subunit and a β-subunit before coating, but need not be cleaved before coating. The protein antigen can be coated directly onto an ELISA plate or bound to a layer of immunoglobulins directly coated onto a plate. For example, soluble isoforms MUC1/X and/or MUC1/Y fusions with immunoglobulin constant regions (Fc) can be bound to anti-Fc antibodies directly coated onto the ELISA plate. The bound protein antigens can then be exposed to the test antibodies.

Antibodies of interest will specifically bind to isoform MUC1/X and/or MUC1/Y, but not to an α-subunit immunogenic tandem repeat region, an α-subunit alone, or a β-subunit alone. Preferably, the antibodies specifically bind to isoform MUC1/X but not to MUC1/Y. Preferably, the antibodies specifically bind to cleaved isoform MUC1/X and cleaved isoform MUC1/TM.

ELISA assay techniques are well known in the art. Texts teaching the practice of ELISA assays include, for example, *The Elisa Guidebook*, by J. R. Crowther (Editor), Humana Pr (August 2000); Delves, *Antibody Applications: Essential Techniques*, John Wiley & Sons (1995); Crowther, *Elisa: Theory and Practice*, Human Pr (1995); Harlow and Lane, *Using Antibodies: A Laboratory Manual*, Cold Spring Harbor Press (1998); and Coligan, et al., *Current Protocols in Immunology*, 1991-2006, John Wiley & Sons.

ELISA techniques are well suited to high throughput methods, whether the test antibodies are directly labeled or a secondary antibody is labeled. The labeled antibody can be labeled with an enzymatic moiety, a chemiluminescent moiety, a fluorescent moiety, or any other conveniently detectable label known in the art. Products for conducting high throughput ELISA are commercially available, for example, from Panomics, Redwood City, Calif.; Sigma-Aldrich, St. Louis, Mo.; and BioMedTech Laboratories, Tampa, Fla. Automated high throughput systems are also commercially available, for example, from Caliper Life Sciences, Hopkinton, Mass.; and BMG Labtech, Durham, N.C.

Flow Cytometry

Antibody binding to intact MUC1 proteins can also be detected using flow cytometry. Intact cells expressing a MUC1 isoform (e.g., MUC1/TM, MUC1/X, MUC1/Y) on their extracellular surface, either naturally occurring or recombinantly modified, can be exposed to the anti-MUC1 α/β antibodies. The cells can be viable or fixed. Binding can be determined by directly labeling the test antibody or a secondary antibody, for example, with a fluorophore. An advantage of using flow cytometry is that the MUC1 antigens expressed on the surface of a cell are in a tridimensional conformation representative of MUC1 cell surface antigens encountered in vivo. Antibodies of interest will specifically bind to the α- and β-subunits of isoforms MUC1/TM and MUC1/X, and preferably will not bind to isoform MUC1/Y. Flow cytometry analysis is also well suited to high throughput methods. Products and systems for high throughput flow cytometry analysis are commercially available, for example, from BD Biosciences, San Jose Calif. and San Diego, Calif.; Beckman Coulter, Fullerton, Calif.; Partec, Münster, Germany; and Amnis Corp., Seattle, Wash.

Flow cytometry techniques are well known in the art. Texts teaching the practice of flow cytometry include, for example, Ormerod, *Flow Cytometry*, Taylor & Francis (1999); *Flow Cytometry Protocols*, Hawley and Hawley (Eds.) Humana Press (2004); and *Flow Cytometry in Clinical Diagnosis*, Keren, et al., (Eds.), ASCP Press (2001).

Immunohistochemistry

Antibody binding to intact MUC1 proteins can also be detected using immunohistochemistry techniques well known in the art. See, for example, Hayat, *Handbook Of Immunohistochemistry And In Situ Hybridization Of Human Carcinomas: Molecular Pathology, Colorectal Carcinoma, And Prostate Carcinoma*, Academic Pr (2004); Hayat, *Immunohistochemistry and in Situ Hybridization of Human Carcinomas: Molecular Genetics Lung and Breast Carcinomas*, Academic Pr (2004); and Dabbs, *Diagnostic Immunohistochemistry*, Elsevier Science Health Science (2001). Epithelial sections from tissues known to express or overexpress a MUC1 antigen, for example, breast, ovarian, prostate, pancreas, colon tissues can be exposed to anti-MUC1 α/β antibodies. The antibodies can be directly labeled, for example, with an enzymatic moiety, a chemiluminescent moiety, a fluorescent moiety. Bound antibody can be detected using microscopy techniques.

Tests for Identifying Anti-MUC1 α/β Antibodies

Anti-MUC1 α/β antibodies of the invention bind to the junction of MUC1 α and β subunits, but do not bind to either the α subunit or the β subunit alone. This can be measured, for example, by conducting a comparative ELISA assay, as described above. ELISA plate wells can be coated with a soluble MUC1 protein antigen having both the α and β subunits (e.g., MUC1/TM, MUC1/X or MUC1/Y) and with MUC1 α-subunit alone, and soluble (i.e., lacking a transmembrane sequence) MUC1 β-subunit alone, and then exposed to anti-MUC1 α/β antibodies. Antibodies of interest will specifically bind to a MUC1 protein antigen having both the α- and β subunits, but will not substantially bind to MUC1 α-subunit alone, or MUC1 β-subunit alone. Alternatively, this could also be measured using a Western Blot. Western Blot methodologies are well known in the art. See, Coligan, et al., supra; and Harlow and Lane, 1989 and 1998, supra.

Preferably, anti-MUC1 α/β antibodies of the invention bind to isoforms MUC1/TM and MUC1/X but do not substantially bind to isoform MUC1/Y. Without being bound to theory, it is believed that cleaved MUC1/X reflects the tridimensional junction of MUC1 α- and β-subunits of a MUC1 protein on the surface of a cell. This can be measured, for example, by conducting a comparative ELISA assay or a comparative flow cytometry assay, as described above. In an exemplified ELISA assay, ELISA plates coated with anti-Fc antibody are bound to MUC1/TM-Fc (i.e., a soluble MUC1 with a full-length α-subunit) or MUC1/X-Fc, and MUC1/Y-Fc fusion proteins and then exposed to anti-MUC1 α/β antibodies. Antibodies of interest will specifically bind to wells with bound MUC1/X-Fc fusion protein or bound MUC1/TM-Fc fusion protein, but will not substantially bind to wells with bound MUC1/Y-Fc fusion protein. See, Example 1, below. Alternatively, this could be measured in a comparative flow cytometry assay, using cells that express one MUC1 isoform on the extracellular surface, naturally or recombinantly. Antibodies of interest will specifically bind to cells that express MUC1/TM or MUC1/X, but will not substantially bind to cells that express MUC1/Y.

Methods of Using Anti-MUC1 α/β Antibodies

Methods of Diagnosis and Prognosis

The anti-MUC1 α/β antibodies find use in methods of diagnosing or providing a prognosis of a cancer of a tissue that overexpresses MUC1. Usually the tissue will be an epithelial tissue, but can also be from blood, for example, plasma cells (i.e., of B lymphocyte lineage, see, e.g., Chapter 98 of *Harrison's Principles of Internal Medicine*, 16th Ed., 2005, McGraw-Hill). The diagnostic and prognostic methods find particular use in identifying MUC1-overexpressing cancers from breast, ovarian, prostate, pancreas, colon, plasma cells and other tissues. A tissue or cell that overexpresses MUC1 will have at least about 20%, 50%, 80%, 1-fold, 2-fold, 3-fold, 4-fold or more detectable MUC1 in comparison to a tissue or cell of the same type from confirmed normal (i.e., non-transformed, non-cancerous) tissue. The diagnostic and prognostic methods conveniently can be carried out using flow cytometry and/or immunohistochemistry methods, described above.

Cancer Immunotherapy Methods

Since MUC1 protein is expressed or overexpressed in many cancers, including but not limited to epithelial and plasma cell myeloma, including breast, ovarian, prostate, pancreas, colon and on the plasma cells of multiple myeloma, it is a target for cancer immunotherapy.

Accordingly, the invention provides anti-MUC1 α/β antibodies that can be used systemically to treat cancer, including breast, ovarian, prostate, pancreas, colon and plasma cell myeloma cancers. Anti-MUC1 α/β antibodies can also be useful in the treatment of various other benign and malignant tumors. Thus, the invention provides a method of treating a patient susceptible to or having a cancer which expresses or overexpresses a MUC1 antigen, comprising administering to said patient a therapeutically effective amount of an antibody which binds specifically to a MUC1 α/β subunit junction. In another approach, the invention provides a method of inhibiting the growth of tumor cells expressing or overexpressing a MUC1 antigen, comprising administering to a patient an antibody which binds specifically to a MUC1 α/β subunit junction in an amount effective to inhibit growth of the tumor cells. Anti-MUC1 α/β antibodies can also be used in a method for selectively inhibiting the growth of or killing a cell expressing or overexpressing a MUC1 antigen comprising reacting an anti-MUC1 α/β antibody immunoconjugate or immunotoxin with the cell in an amount sufficient to inhibit the growth of or kill the cell.

For example, unconjugated anti-MUC1 α/β antibody (including monoclonal, polyclonal, chimeric, humanized, fully human and fragments thereof (e.g., recombinant proteins)) can be introduced into a patient such that the antibody binds to an intact MUC1 protein on cancer cells and mediates growth inhibition of such cells (including the destruction thereon, and the tumor, by mechanisms which may include complement-mediated cytolysis, antibody-dependent cellular cytotoxicity, altering the physiologic function of MUC1, and/or the inhibition of ligand binding or signal transduction pathways. In addition to unconjugated anti-MUC1 α/β antibodies, fragments thereof, and recombinant proteins of the invention, anti-MUC1 α/β antibodies conjugated to toxic agents, including radioisotopes, ricin and/or pseudomonas toxin, can also be used therapeutically to deliver the toxic agent directly to MUC1-bearing tumor cells and thereby destroy the tumor.

Cancer immunotherapy using anti-MUC1 α/β antibodies can follow the teachings generated from various approaches which have been successfully employed with respect to several types of cancer, including but not limited to colon cancer (Arlen et al., 1998, *Crit Rev Immunol* 18: 133-138). multiple myeloma (Ozaki et al., 1997, *Blood* 90: 3179-3186; Tsunenari et al., 1997, *Blood* 90: 2437-2444), gastric cancer (Kasprzyk et al., 1992, *Cancer Res* 52: 2771-2776), B-cell lymphoma (Funakoshi et al., 1996, *J Immunther Emphasis Tumor Immunol* 19: 93-101), leukemia (Zhong et al., 1996, *Leuk Res* 20: 581-589), colorectal cancer (Moun et al., 1994, *Cancer Res* 54: 6160-6166); Velders et al., 1995, *Cancer Res* 55: 4398-4403), and breast cancer (Shepard et al., 1991, *J Clin Immunol* 11: 117-127). Further examples of immunotoxin therapy against cancers are reviewed in, for example, Wong, et al., *Semin Oncol* (2005) 32:591; Chen, et al., *Expert Opin Drug Deliv* (2005) 2:873; and Li, et al., *Cell Mol Immunol* (2005) 2:106.

For example, one way to apply anti-MUC1 α/β antibodies clinically is to administer them in umnodified form, using monoclonal anti-MUC1 α/β antibodies which display antitumor activity (e.g., ADCC and CDC activity) and/or internalizing ability in vitro and/or in animal models (see, e.g. Hellstrom et al., *Proc. Natl. Acad. Sci. USA* 82:1499-1502 (1985). To detect ADCC and CDC activity monoclonal antibodies can be tested for lysing cultured $^{51}$Cr-labeled tumor target cells over a 4-hour incubation period. Target cells are labeled with $^{51}$Cr and then can be exposed for 4 hours to a combination of effector cells (in the form of human lymphocytes purified by the use of a lymphocyte-separation medium) and antibody, which is added in concentrations, e.g., varying between 0.1 µg/ml and 10 µg/ml. The release of $^{51}$Cr from the target cells is measured as evidence of tumor-cell lysis (cytotoxicity). Controls include the incubation of target cells alone or with either lymphocytes or monoclonal antibody separately. The total amount of $^{51}$Cr that can be released is measured and ADCC is calculated as the percent killing of target cells observed with monoclonal antibody plus effector cells as compared to target cells being incubated alone. The procedure for CDC is identical to the one used to detect ADCC except that human serum, as a source of complement, (diluted 1:3 to 1:6) is added in place of the effector cells.

In the practice of the method of the invention, anti-MUC1 α/β antibodies capable of inhibiting the growth of cancer cells expressing or overexpressing MUC1 on the cell surface are administered in a therapeutically effective amount to cancer patients whose tumors express or overexpress MUC1. The antibody therapy methods of the invention may be combined with a chemotherapeutic, radiation, and/or other therapeutic regimen.

Anti-MUC1 α/β antibodies useful in treating cancer include those which are capable of initiating a potent immune response against the tumor and those which are capable of direct cytotoxicity. In this regard, anti-MUC1 α/β antibodies can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites or complement proteins. In addition, anti-MUC1 α/β antibodies which exert a direct biological effect on tumor growth are useful in the practice of the invention. Such antibodies may not require the complete immunoglobulin to exert the effect. Potential mechanisms by which such directly cytotoxic antibodies may act include inhibition of cell growth, modulation of cellular differentiation, modulation of tumor angiogenesis factor profiles, and the induction of apoptosis. The mechanism by which a particular anti-MUC1 α/β antibody exerts an anti-tumor effect can be evaluated using any number of in vitro assays designed to determine ADCC, ADMMC, complement-mediated cell lysis known in the art. See, for example, *Current Protocol in Immunology*, supra.

The anti-tumor activity of a particular anti-MUC1 α/β antibody, or combination of anti-MUC1 α/β antibodies, is preferably evaluated in vivo using a suitable animal model. Xenogenic cancer models, wherein human cancer explants or passaged xenograft tissues are introduced into immune compromised animals, such as nude or SCID mice, are particularly appropriate and are known. For example, xenograft models of human prostate cancer (capable of recapitulating the development of primary tumors, micrometastasis, and the formation of osteoblastic metastases characteristic of late stage disease) are described in Klein et al., 1997, *Nature Medicine* 3: 402-408 and in PCT Patent Application WO 98/16628, Sawyers et al., published Apr. 23, 1998. The examples herein provide detailed experimental protocols for evaluating the anti-tumor potential of anti-MUC1 α/β antibodies preparations in vivo. Other in vivo assays are contemplated such as those which measure regression of established tumors, interference with the development of metastasis, and the like.

It should be noted that the use of murine or other non-human and chimeric (monoclonal) antibodies may induce moderate to strong immune responses in some patients. In the most severe cases, such an immune response may lead to the extensive formation of immune complexes which, potentially, can cause renal failure. Accordingly, preferred (monoclonal) antibodies used in the practice of the therapeutic methods of the invention are those which are either fully human or humanized and which bind specifically to the target intact MUC1 antigen with high affinity but exhibit low or no antigenicity in the patient.

The methods of the invention contemplate the administration of single anti-MUC1 α/β antibodies, as well as combinations, or "cocktails," of different individual (monoclonal) antibodies, such as those recognizing different epitopes. Such antibody cocktails may have certain advantages inasmuch as they contain antibodies which bind to different epitopes and/or exploit different effector mechanisms or combine directly cytotoxic antibodies with antibodies that rely on immune effector functionality. Such antibodies in combination may exhibit synergistic therapeutic effects. In addition, the administration of anti-MUC1 α/β antibodies can be combined with other therapeutic agents, including but not limited to various chemotherapeutic agents, androgen-blockers, immune modulators (e.g., IL-2, GM-CSF), other therapeutic antibodies (e.g., against other epitopes on MUC1, against tumor associated antigens other than MUC1, against other therapeutically useful epitopes), and agents against infectious and other diseases. The anti-MUC1 α/β antibodies can be administered in their "naked" or unconjugated form, or can have therapeutic agents conjugated to them.

The anti-MUC1 α/β antibodies used in the practice of the methods of the invention can be formulated into pharmaceutical compositions comprising a physiologically compatible carrier suitable for the desired delivery method. Suitable carriers include any material which when combined with the anti-MUC1 α/β antibodies retains the anti-tumor function of the antibody and is non-reactive with the subject's immune systems. Examples include, but are not limited to, any of a number of standard pharmaceutical carriers such as sterile phosphate buffered saline solutions, bacteriostatic water, and the like (see, generally, *Remington: The Science and Practice of Pharmacy*, Gennaro (Editor) Lippincott Williams & Wilkins (2003).

The anti-MUC1 α/β antibody formulations can be administered via any route capable of delivering the antibodies to the tumor site. Potentially effective routes of administration include, but are not limited to, intravenous, intraperitoneal, intramuscular, intratumor, intradermal, and the like. The preferred route of administration is by intravenous injection. A preferred formulation for intravenous injection comprises the anti-MUC1 α/β antibodies in a solution of preserved bacteriostatic water, sterile unpreserved water, and/or diluted in polyvinylchloride or polyethylene bags containing 0.9% sterile Sodium Chloride for Injection, USP. The anti-MUC1 α/β antibody preparation can be lyophilized and stored as a sterile powder, preferably under vacuum, and then reconstituted in bacteriostatic water containing, for example, benzyl alcohol preservative, or in sterile water prior to injection.

Treatment will generally involve the repeated administration of the anti-MUC1 α/β antibody preparation via an acceptable route of administration such as intravenous injection (IV), at an effective dose. Dosages will depend upon various factors generally appreciated by those of skill in the art, including without limitation the type of cancer and the severity, grade, or stage of the cancer, the binding affinity and half life of the antibody or antibodies used, the degree of MUC1 expression in the patient, the extent of circulating shed MUC1 α-subunit antigen, the desired steady-state antibody concentration level, frequency of treatment, and the influence of chemotherapeutic agents used in combination with the treatment method of the invention. Typical daily doses may range from about 0.1 to 100 mg/kg. Doses in the range of 10-500 mg antibody per week can be effective and well tolerated, although even higher weekly doses can be appropriate and/or well tolerated. The principal determining factor in defining the appropriate dose is the amount of a particular antibody necessary to be therapeutically effective in a particular context. Repeated administrations can be required in order to achieve tumor inhibition or regression. Initial loading doses can be higher. The initial loading dose can be administered as an infusion. Periodic maintenance doses can be administered similarly, provided the initial dose is well tolerated.

Direct administration of anti-MUC1 α/β antibodies is also possible and may have advantages in certain contexts. For example, for the treatment of ovarian carcinoma, anti-MUC1 α/β antibodies can be injected directly into the intraperitoneal space.

Attaching Biologically Active Compositions to the Antibodies

The procedure for attaching a biologically active component (e.g., a cytotoxic moiety) to an antibody will vary according to the chemical structure of the component. Generally, the antibodies will contain a variety of functional groups which are available for reaction with a suitable functional group on a biologically active molecule to bind the agent thereto. Alternatively, the antibody and/or biologically active component may be derivatized to expose or attach additional reactive functional groups. The derivatization may involve attachment of any of a number of linker molecules such as those available from Pierce Chemical Company, Rockford Ill. A "linker" as used herein refers to a molecule used to join, covalently or non-covalently, the antibody and biologically active component. Suitable linkers are well known to those of skill in the art and include, but are not limited to, straight or branched-chain carbon linkers, heterocyclic carbon linkers, or peptide linkers. See, e.g., Birch and Lennox, *Monoclonal Antibodies: Principles and Applications*, Chapter 4, Wiley-Liss, New York, N.Y. (1995); U.S. Pat. Nos. 5,218,112, 5,090,914; Hermanson, *Bioconjugate Techniques*, Academic Press, San Diego, Calif. (1996).

Where both molecules are polypeptides, the linkers may be joined to the constituent amino acids through their side groups (e.g., through a disulfide linkage to cysteine). A bifunctional linker having one functional group reactive with a group on a particular biologically active component, and another group reactive with a antibody, can be used to form the desired conjugate. In some embodiments, a bifunctional linker can be used to join two antibodies, for example, an anti-MUC1 α/β antibody and another antibody. Alternatively, derivatization may involve chemical treatment of the component; e.g., glycol cleavage of the sugar moiety of the glycoprotein antibody with periodate to generate free aldehyde groups. The free aldehyde groups on the antibody may be reacted with free amine or hydrazine groups on an agent to bind the agent thereto. (See, U.S. Pat. No. 4,671,958). Procedures for generation of free sulfhydryl groups on antibodies or antibody fragments are also known (See, U.S. Pat. No. 4,659,839). Many procedures and linker molecules for attachment of various compounds including radionuclide metal chelates, toxins and drugs to proteins such as antibodies are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. *Cancer Res.* 47: 4071-4075 (1987)). Chemical linkers are commercially available, for example, from Pierce Biotechnology, Rockford, Ill.

It is sometimes desirable to release the conjugated molecule when it has reached a target site. Therefore, conjugates comprising linkages which are cleavable in the vicinity of the target site may be used. Cleaving of the linkage to release the biologically active component from the antibody may be prompted by enzymatic activity or conditions to which the conjugate is subjected either inside the target cell or in the vicinity of the target site. When the target site is a tumor, a linker which is cleavable under conditions present at the tumor site (e.g. when exposed to tumor-associated enzymes or acidic pH) may be used. Use of the cis-aconitic acid spacer is useful for releasing biologically active components in endosomes. Similarly, disulfide linkages are cleavable in the reductive environment of the endosomes.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 5,141,648 discloses immunoconjugates comprising linkers of specified chemical structure, wherein the linkage is cleaved in vivo thereby releasing the attached compound (radiotherapeutic agent, drug, toxin, etc.). The linker is susceptible to cleavage at a mildly acidic pH, and is believed to be cleaved during transport into the cytoplasm of a target cell, thereby releasing the biologically active compound inside a target cell. U.S. Pat. No. 4,671,958 includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other components to antibodies one skilled in the art will be able to determine a suitable method for attaching a given component to a antibody of the present invention.

Methods of Stimulating an Immune Response Against an Antigen of Interest

The present invention also provides methods for eliciting an immune response or improving an immune response or raising antibodies against any antigen of interest by immunizing a subject capable of producing antibodies (i) first, one or more times with a MUC1 antigen comprising an immunogenic tandem repeat sequence and an antigen of interest; and (ii) second, boosting one or more times with the antigen of interest. The MUC1 antigen and the antigen of interest independently can be administered as a polypeptide or a nucleic acid encoding the polypeptide. The MUC1 antigen and the antigen of interest can be administered concurrently as unconnected molecules, as molecules attached by a linker (described above), or as a fusion protein.

The antigen of interest can be any antigenic sequence, including without limitation antigenic sequences of human, mammal, animal, plant, bacterial, viral or synthetic origin.

An antigen of interest can include any tumor associated antigen, including oncofetal antigens, oncogene products, tissue-lineage antigens, viral antigens. Exemplified tumor associated antigens include carcinoembryonic antigen (CEA), carbohydrate antigen (CA-125), MUC1, prostate-specific membrane antigen (PSMA), prostate stem cell antigen (PSCA), prostate-specific antigen (PSA), melanocyte antigens (e.g., MART-1/Melan A, tyrosinase, gp100, and TRP-1 (gp75)), oncofetal antigen (OFA), Her2/neu.

An antigen of interest can be an infectious disease-associated antigen, for example, from a parasite, a bacterium, a virus. For example, antigens useful in mounting an immune response against malaria are described, for example, in *The Intolerable Burden of Malaria: II. What's New, What's Needed*, Breman, et al., editors, The American Society of Tropical Medicine and Hygiene (2004). Antigens useful in eliciting an antibody response against HIV are described, for example, in Burton, et al., *Proc Natl Acad Sci USA*. (2005) 102:14943.

EXAMPLES

The following examples are offered to illustrate, but not to limit the claimed invention.

Example 1

Production of an anti-MUC1 α/β antibody

The following example demonstrates production of anti-MUC1 α/β antibodies by first immunizing with a MUC1/TM cDNA antigen and then boosting with an extracellular domain of a MUC1/X protein antigen. Antibodies were selected by screening for those that bound to a MUC1/X-immunoglobulin constant region fusion protein in an ELISA assay.

Experimental Procedures

Materials and antibodies. Reagents and chemicals were obtained from Sigma (St Louis, Mo.), unless otherwise specified. The anti-MUC1 tandem-repeat antibodies (anti-EMA, epithelial membrane antigen, Mc5) were obtained from Chemicon International (Temeluca, Calif.).

Cell Culture. Cells were grown at 37° C. and 5% $CO_2$, in culture media supplemented with 10% heat inactivated fetal calf serum, 2 mM L-glutamine, 100 IU/ml penicillin and 25 μg/ml streptomycin. DA3 mouse mammary tumor cells and HK293, human embryonic kidney cells, were grown in Dulbecco's modified Eagle's medium (DMEM). Expression constructs were transfected into the cells using the calcium phosphate procedure.

Generation of stable DA3 mouse mammary tumor cell transfectants expressing MUC1/TM. DA3 cells were co-transfected with the eucaryotic expression plasmids pCL-MUC1/TM (or pCL-MUC/TM truncated at the cytoplasmic PvuII site) and pSV2neo (coding for neomycin resistance). Stable transfectants were selected with neomycin. Transfectants expressing the MUC1 proteins were identified by immunoblot analysis of cell lysates using affinity purified polyclonal antibodies directed against the MUC1 cytoplasmic domain.

Generation of MUC1/X and MUC1/Y eucaryotic expression constructs and fusion proteins. MUC1 antigen polypeptides employed in this study include a MUC1/X-immunoglobulin constant chain fusion protein ("Flag-Yex-hFc") and a MUC1/Y-immunoglobulin constant chain fusion protein ("Flag-Xex-hFc"), depicted and described in FIG. 1 and Levitin, et al., supra). Standard molecular biology methods were used to generate all constructs, as previously described (see, Levitin, et al., supra).

Generation of HK293 transfectants expressing Flag-MUC1/Xex-hFc and Flag-MUC1/Yex-hFc fusion proteins and purification of hFc-tagged fusion proteins. HK293 (human kidney) cells were transiently transfected using calcium phosphate with the eucaryotic pCMV3 expression vectors (6

μg DNA/25 cm² flask) coding for the Flag-Xex-hFc, Flag-Yex-hFc or mutant MUC1/X proteins. For obtaining stable transfectants, neomycin resistant clones were isolated following addition of neomycin to the culture medium. Conditioned media (CM) containing the secreted MUC1 fusion proteins were spun at 15,000 rpm for 20 minutes, and the supernatant filtered through 0.45 μm filters and stored at −75° C. Protein A-Sepharose 4 Fast Flow (AmershamPharmacia Biotech, Piscataway, N.J.) was used to purify the C-terminally hFc tagged Flag-Xex(Yex)-hFc proteins.

ELISA assay for determining binding of anti-MUC1 antibodies (hybridoma supernatants) to the MUC1/X (MUC1/Y) proteins and to the MUC1 α/β junction. ElisaImmunoAssay plates (Costar, Corning, N.Y.) were coated with polyclonal goat anti-human Fc (Gα-hFc, 4 μg/ml) followed by washing with PBS-Tween20 (0.05%) and blocking with PBS-Tween+ 5% skimmed milk (Blotto). Spent culture media containing Flag-Xex(or Yex)-hFc proteins (mutant and wild type) was then applied to the wells to allow for binding of the Flag-Xex (Yex)-hFc proteins. Following incubation, samples were removed and the wells washed with PBS/Tween. Wells were then incubated with the mouse monoclonal antibodies (or hybridoma supernatants) followed by HRP-conjugated anti-mouse antibody.

Immunization of mice and hybridoma production. Mice were immunized with consecutive intradermal DNA immunizations spaced at 21 day intervals. DNAs injected were either pCL-MUC1/TM or pCL-MUC1/X expression vector plasmids. Finally the mice were boosted with the extracellular domain of the MUC1/X protein injected with incomplete Freund's adjuvant. Hybridomas were prepared by fusion of the myeloma cell line with immune splenocytes and screened by ELISA assay (see above).

Results

Immunization with MUC1/TM cDNA but not with MUC1/X cDNA induces anti-MUC1 α/β junction antibodies. Mice were immunized with expression vectors containing cDNA coding for either the MUC1/TM protein containing the α chain tandem repeat array or with cDNA coding for the MUC1/X isoform from which the tandem repeat is deleted (FIG. 1). Following four consecutive DNA immunizations, sera were assayed for antibody directed against MUC1/X. The MUC1/X isoform which is cleaved at an identical site as the full-length MUC1/TM molecule served as the screening protein to identify anti-MUC1 α/β junction antibodies. This provided several advantages. Because the MUC1/X extracellular domain lacks the central tandem repeat array, antibodies directed against the highly immunogenic tandem repeat array epitopes will not be detected. More importantly, as MUC1/X is composed solely of two small interacting MUC1/X α and β subunits that form the native α/β junction, only antibodies directed against epitopes common to both MUC1/X and MUC1/TM will be detected. The native MUC1 α/β junction is one such major epitope, making this screening procedure a simple detection system for antibodies binding this critical region of interest.

Unexpectedly, all mice (five out of five) immunized with the MUC1/X cDNA failed to raise significant anti-MUC1/X antibody titers (FIGS. 2A and B). In contrast, five out of five mice immunized with MUC1/TM cDNA generated highly reproducible, albeit modest, anti-MUC1/X antibody titers (FIGS. 2A and B). These results indicated that whereas immunization with MUC1/TM cDNA could induce antibodies that recognize epitopes common to both the MUC1/X and MUC1/TM proteins, immunization with MUC1/X cDNA elicited only modest titers of anti-MUC1/X antibodies.

As our primary objective was to generate monoclonal antibodies recognizing the α/β junction, mice with much higher anti-MUC1/X titers were required. In order to generate high-titer anti-MUC1/X, we boosted the MUC1/TM cDNA-primed mice with MUC1/X protein. Following a single MUC1/X protein boost all immunized mice showed a hundred-fold increase in anti-MUC1/X titers, from 1:300 (after the MUC1/TM cDNA immunization alone) to a minimum of 1:30,000 following the MUC1/X protein boost (FIGS. 3A-D). High titers were observed eighteen days following the MUC1/X protein boost which increased even higher at day 32 (FIGS. 3A-D). Remaining mice not sacrificed for use in hybridoma formation sustained high anti-MUC1/X protein titers even six months following the initial single MUC1/X protein boost. To best generate anti-α/β junction specific antibodies, we proceeded to hybridoma formation using spleen cells from mice showing the highest anti-MUC1/X antibody titers.

Generation of DMC209 monoclonal antibodies that recognize the cleaved α/β junction. Spent media from ten 96-well plates containing fused spleen-myeloma cells were assayed for antibodies recognizing the cleaved MUC1 α/β junction. To identify such antibodies, hybridoma supernatants were screened in parallel against the cleaved MUC1/X protein and the structurally similar, but uncleaved MUC1/Y isoform (FIG. 1). Whereas MUC1/X is cleaved at an identical site as in the full-length MUC1/TM protein resulting in interacting α and β subunits, MUC1/Y which does not cleave does not contain the MUC1 α/β junction epitope. We selected for hybridomas that were MUC1/X-positive and MUC1/Y-negative.

Screening nine hundred and fifty hybridoma supernatants yielded two hybridomas highly reactive with MUC1/X protein, but non-reactive with MUC1/Y. Limiting cell dilution resulted in pure clones which were designated DMC209, an IgM antibody, and DMC111, an Igγ2a antibody.

Figure 4:
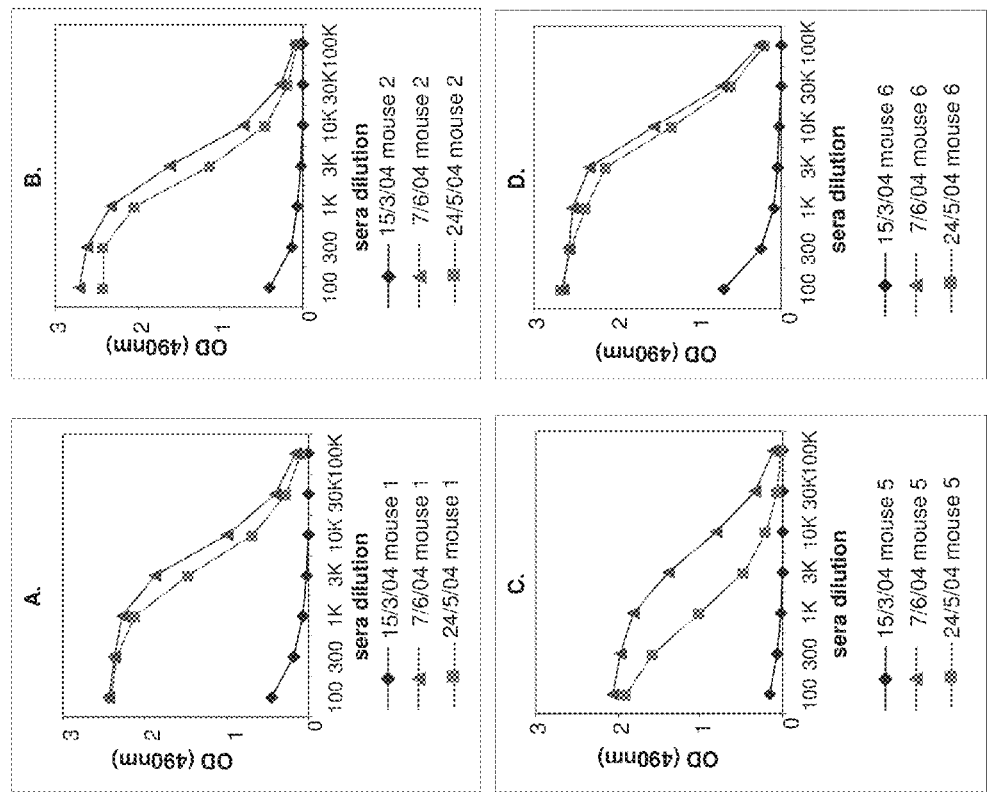
FIGS. 4A-D illustrate anti-MUC1/X titers in mice primed with MUC1/TM cDNA followed by a single MUC1/X protein boost. Group II mice previously primed with MUC1/TM cDNA immunizations (see, FIG. 2) were boosted with a single MUC1/X protein immunization. Sera were assayed for anti-MUC1/X reactivity, as described in the Examples, eighteen or thirty two days (pink and green lines, respectively) following the protein boost. Titers for individual mice are presented.

Detailed epitope analysis of DMC209 and DMC111 reactivity. Analysis of the specificity of the monoclonal antibodies generated by cloned DMC209 and DMC111 confirmed that both were MUC1/X positive and MUC1/Y (=Δ 1-18, FIG. 4B) negative. Furthermore, DMC209 and DMC111 were also nonreactive with the non-cleaved Δ 1-11 protein (FIG. 4F) but reacted with cleaved Δ1-7 MUC1/X protein (FIG. 4E). Additional analyses showed that whereas DMC209 and DMC111 bound equally well to the wild type MUC1/X protein and to the cleaved S63→C and S63→T mutant proteins (FIG. 4C), all other S63 mutant uncleaved MUC1/X proteins (FIG. 4D) were completely non-reactive with DMC209. In contrast, DMC111 reacted equally well with both the cleaved MUC1/X proteins (wild type and cleaved S63→C and S63→T mutant proteins, FIG. 4D) and with the uncleaved S63 mutant proteins (FIG. 4D). These results confirm that the epitopes recognized by the two monoclonal antibodies are different. More importantly, only DMC209 is completely dependent on MUC1 cleavage for its reactivity. Significantly, DMC209 was non-reactive with both the MUC1 α-subunit and β-subunits when each was tested in isolation; DMC209 reacts with the two subunits only when presented as interacting entities. These analyses provided strong evidence that DMC209 (i) is cleavage-dependent and (ii) recognizes the junction of the interacting α-subunit and β-subunit. Further analyses (described below) revealed robust binding of DMC209 to cells expressing MUC1/TM, the major MUC1 isoform and significantly less binding with the non-cleavage dependent DMC111 antibody. Henceforth our reported analyses are restricted to the cleavage-dependent antibody DMC209.

Figure 5:
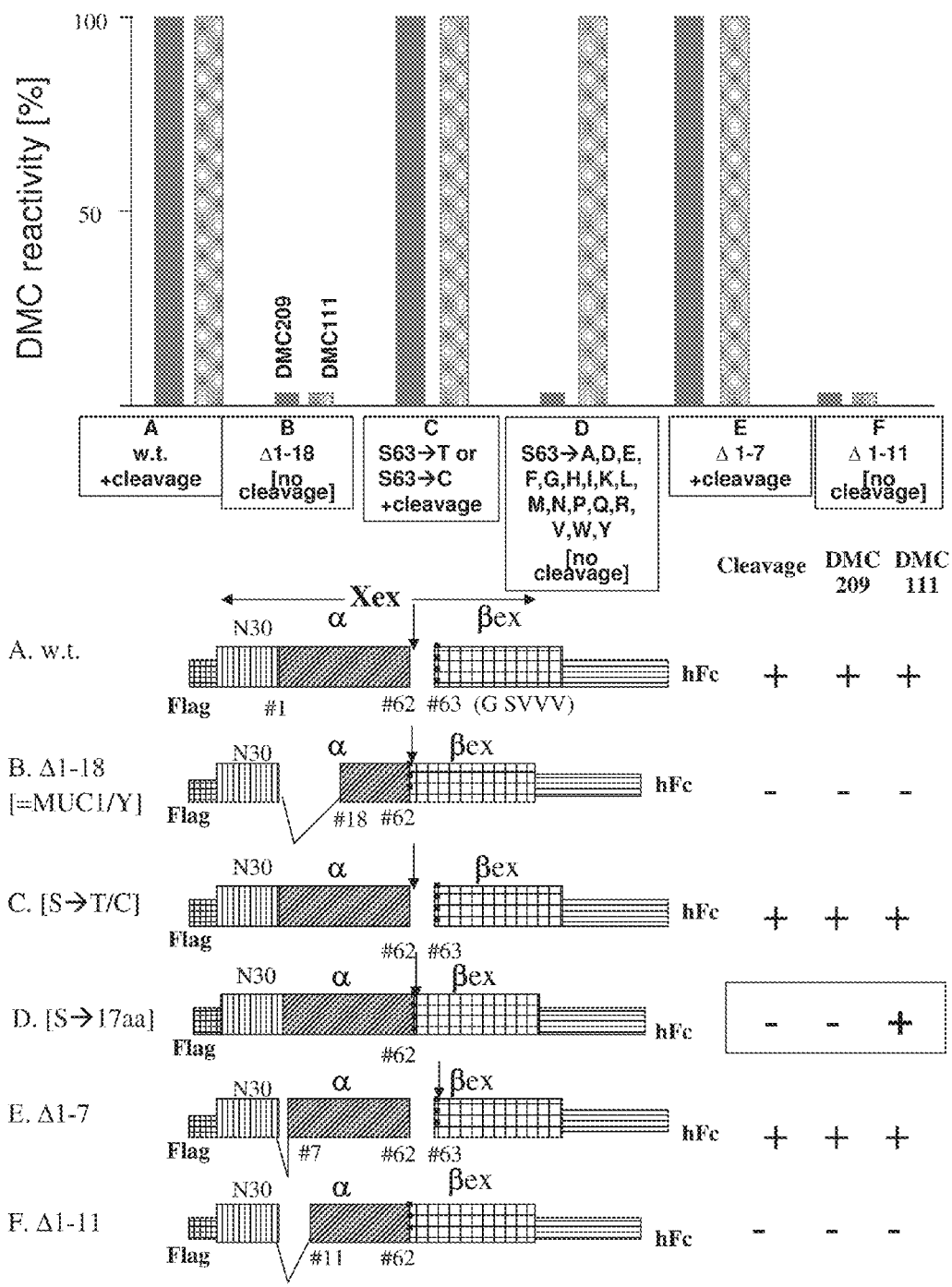
FIG. 5 illustrates detailed analysis of the epitopes recognized by DMC209 and DMC111 monoclonal antibodies. Wild type MUC1/X and MUC1/Y proteins (A and B) as well as point-mutated MUC1/X (C and D) and internally-deleted MUC1/X (E and F) were assayed for their reactivity with the DMC209 and DMC111 antibodies, as described in the Examples. GSVVV=SEQ ID NO:14.

Binding of DMC209 to MUC1/TM on intact cells. MUC1/TM is the major MUC1 protein of all MUC1 isoforms, and is composed of an α-subunit containing a large tandem repeat array bound non-covalently to a membrane-tethered α-subunit. It is expressed at high levels by cells in a wide range of adenocarcinomas as a cell surface heterodimer (FIG. 1). Since DMC209 recognizes the cleaved α/β junction located in the MUC1/X protein and as this cleavage site has been shown to be identical to that found in the full-length MUC1/TM protein, it was of critical importance to determine whether DMC209 binds to the MUC1/TM protein displayed on intact cells. We approached this issue by first examining whether mouse cells not expressing human MUC1/TM become reactive with DMC209 following transfection with human MUC1/TM. Whereas non-transfected parental mouse mammary tumor cells were completely non-reactive with DMC209 (FIG. 5A), DMC209 clearly bound to the same cells expressing either the full-length MUC1/TM protein (FIG. 5B) or an isoform lacking the cytoplasmic domain of MUC1/TM (FIG. 5C). To confirm that MUC1/TM is expressed on these cells, controls done with antibody to the α-chain tandem-repeat-array demonstrated, as expected, MUC1 expression on the transfected cells (FIG. 5II).

Having established that the DMC209 mAbs bound MUC1/TM in transfected cells, we proceeded to investigate whether these antibodies also bind tumor cell lines known to express MUC1/TM. HEY (an ovarian cancer cell line), and the breast cancer cell lines T47D and MDA231 all demonstrated significant DMC209 binding (FIGS. 5C, D and E, respectively).

DMC209 binds MUC1-expressing multiple myeloma cells in fresh bone marrow aspirates. For ultimate clinical application, antibodies to the MUC1 α/β junction must be able to target MUC1-expressing malignant cells. To investigate whether DMC209 antibodies can selectively bind tumor cells in an in vivo-like setting, malignant plasma cells in freshly obtained bone marrow aspirates from patients with multiple myeloma were used. The heterogeneous cell population in the aspirates allows direct assessment of DMC209 binding specificity. DMC209 should bind multiple myeloma cells, known to highly express MUC1 while not bind, or minimally bind, non-MUC1 expressing cells present in the same aspirate sample. Furthermore, DMC209 cell binding in the aspirate material can be readily compared with simultaneous staining with anti-syndecan (CD138), a well-recognized myeloma marker.

Figure 6:
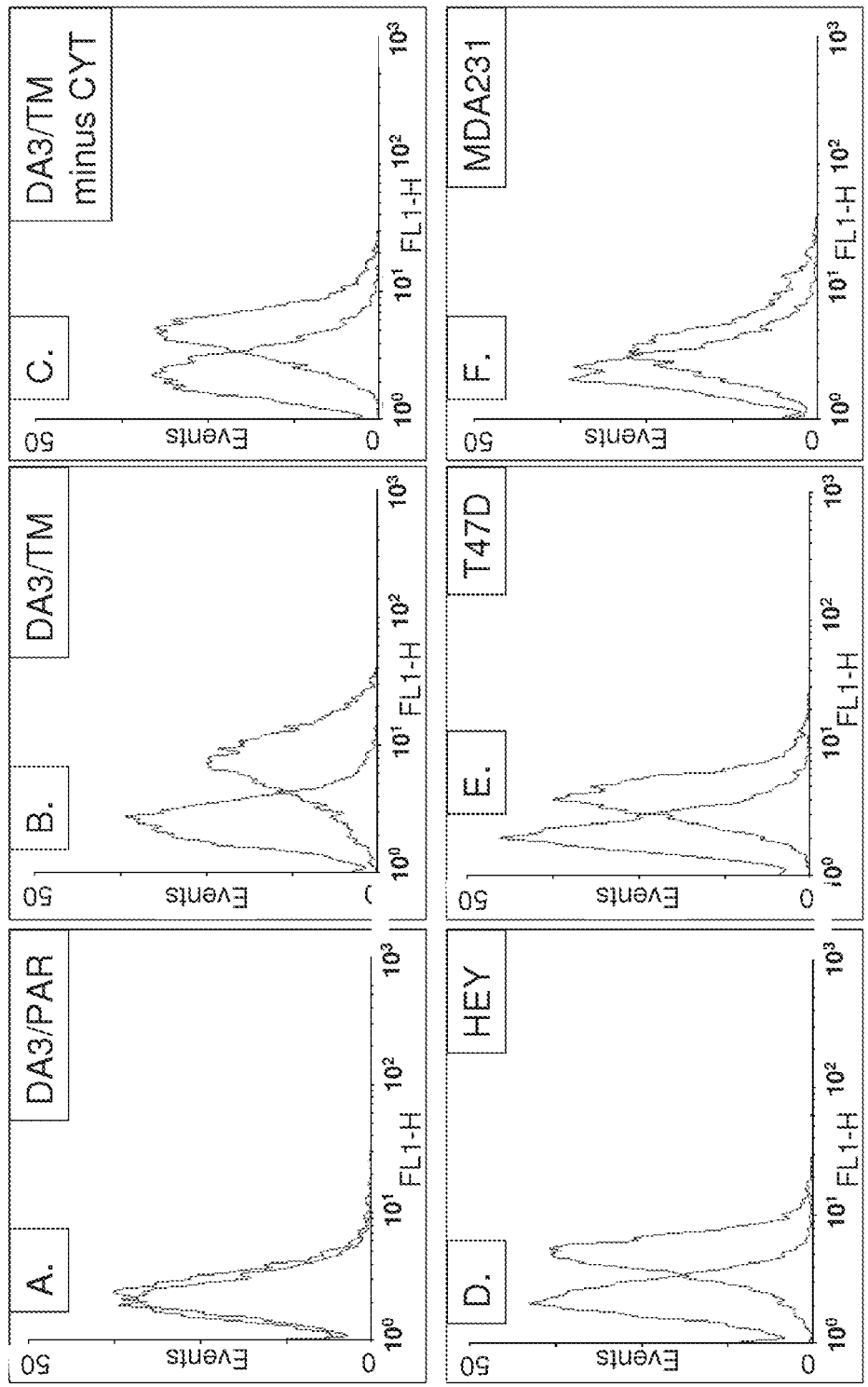
FIGS. 6A-F illustrate DMC209 flow cytometry analyses of MUC1/TM expressing cells. Parental non-transfected mouse mammary tumor cells, or cells transfected with cDNA coding for full-length MUC1/TM or MUC1/TM with its cytoplasmic-tail truncated (DA3/PAR, DA3/TM and DA3/TM minus CYT, respectively) were reacted with DMC209 and analyzed by flow cytometry, as described in the Examples. Similarly, the ovarian cancer cell line HEY and breast cancer cells cell lines T47D and MDA231 were analyzed following incubation with DMC209. The red and purple tracings represent reaction of cells with the fluorescently-labeled secondary antibody alone or with primary DMC209 antibody followed by secondary antibody, respectively.
Figure 7:
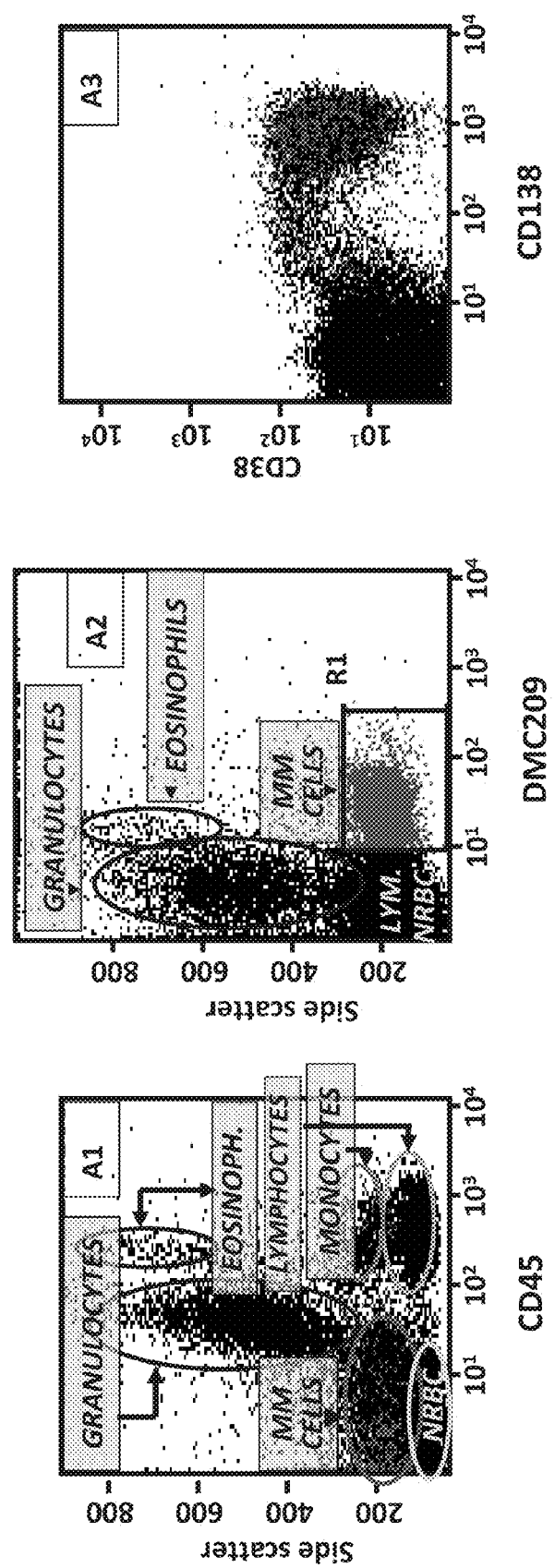
FIG. 7 illustrates flow cytometry analysis of DMC209 reactivity with freshly-obtained bone marrow cells from patients with multiple myeloma. Bone marrow aspirate was simultaneously analyzed with DMC209 and with antibodies to CD45, CD138, and CD38. The antibodies were separately labeled with fluorochromes, each fluorescing with a different emission wavelength. Side scatter analyses were performed against CD45 (A1) and DMC209 (A2). The DMC209 positive cells were designated R1, and the plot of CD38-positive cells versus CD138-positive cells (A3) clearly shows that the DMC209-positive population (red labeled cells) is concordant with CD138-positive cells.

Plotted side scatter (reflecting cell granularity) versus CD45 positive cells assessed the composition of the mixed cell populations present in the bone marrow aspirate (FIG. 6A). This confirmed that the bone aspirate material consisted of the expected heterogeneous cell populations including granulocytes, eosinophils, lymphocytes, monocytes, nucleated red blood cells and malignant plasma (myeloma) cells (FIG. 6A). A simultaneous analysis with red-fluorescently labeled DMC209 antibodies revealed a discrete population of cells that showed significant DMC 209 reactivity. This selected population, designated R1 (FIG. 6B), showed complete concordance with antibodies to syndecan-CD138, (FIG. 6C). Similar results were obtained with an additional three out of three freshly-obtained bone marrow aspirates from patients with multiple myeloma. The recognition of the MUC1-expressing malignant plasma cells and lack of binding to the non-MUC1 expressing cell lineages in the same fresh, unmanipulated aspirate sample underscores the exquisite specificity of the DMC209 anti-α/β junction antibodies in distinguishing MUC1-expressing tumor cells.

Immunohistochemical staining of breast cancer tissue with DMC209 anti-α/β junction antibodies. To visualize DMC209 immunoreactivity with MUC1 expressing tumor cells present in breast cancer tissue an immunohistochemical analysis was performed on malignant breast tissue and normal breast tissue, both obtained from the same surgically excised sample. In parallel, the sections were immunohistochemically analyzed with an antibody that recognizes the MUC1 tandem repeats (α-EMA-anti epithelial membrane antigen, see Experimental Procedures). Both α-EMA and the DMC209 anti-α/β junction antibodies, reacted strongly with the malignant breast cancer cells. Significantly less staining was observed in the non-malignant, normal breast tissue.

We next performed simultaneous double staining with the DMC209 and anti-tandem-repeat antibodies, fluorescently labeled red and green respectively. MUC1 immunoreactivity was readily detected in frozen sections of malignant breast tissue using red-labeled DMC209. Strong anti-MUC1 immunoreactivity was seen on the malignant breast epithelial cells and essentially all immunoreactivity was competed out by adding unlabeled DMC209 antibody, hence validating the specificity of immunoreactivity. No staining was seen in fibroblasts embedded within the connective tissue nor within the connective tissue itself. As expected, green labeling representing immunoreactivity with the anti-tandem-repeat antibodies co-localized with that seen for the red-labeled DMC209.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated MUC1-specific antibody that binds specifically to the α/β subunit junction of an intact MUC1/TM protein with the proviso that the antibody does not substantially bind to the α subunit in the absence of the β subunit and does not substantially bind to the β subunit in the absence of the α subunit.

2. The antibody of claim 1, wherein the antibody binds to isoform MUC1/X but does not substantially bind to isoform MUC1/Y.

3. The antibody of claim 1, wherein the antibody is a monoclonal antibody.

4. The antibody of claim 1, wherein the antibody has a titer of from about 1:300 to about 1:30,000.

5. The antibody of claim 1, wherein the antibody is an IgM.

6. The antibody of claim 1, wherein the antibody is an IgG.

7. The antibody of claim 1, wherein the antibody is humanized.

8. The antibody of claim 1, wherein the antibody is human.

9. The antibody of claim 1, wherein the antibody is a recombinant single chain variable region fragment of an antibody.

10. The antibody of claim 1, further comprising a cytotoxic moiety.

11. The antibody of claim 1, further comprising a label moiety.

12. The antibody of claim 1, wherein the antibody prevents the disassociation of the α subunit from the β subunit.

13. An isolated cell producing an antibody of claim 1.

14. The cell of claim 13, wherein the cell is a hybridoma cell.

15. The antibody of claim 1 for use in a method of targeting an immunotoxin to a cancer cell overexpressing MUC1, the method comprising administering the antibody conjugated to a toxic agent.

16. A method of producing a MUC1-specific antibody that binds to the α/β subunit junction of an intact MUC1/TM protein, comprising the steps of:
   i) immunizing a non-human mammal with a MUC1/TM antigen including the α subunit tandem repeats in an amount sufficient to yield a MUC1-specific antibody that binds specifically to the intact MUC1 protein;
   ii) immunizing the non-human mammal with a MUC1/X antigen;
   iii) selecting for antibodies that bind to a MUC1/X polypeptide; and
   iv) selecting for antibodies that do not substantially bind to isoform MUC1/Y;
   wherein the antibody does not substantially bind to the α subunit in the absence of the β subunit and does not substantially bind to the β subunit in the absence of the α subunit.

17. The method of claim 16, wherein the MUC1/TM antigen is a MUC1/TM polypeptide.

18. The method of claim 16, wherein the MUC1/TM antigen is a nucleic acid encoding a MUC1/TM polypeptide.

19. The method of claim 16, wherein the MUC1/X antigen is a MUC1/X polypeptide.

20. The method of claim 16, wherein the MUC1/X antigen is a nucleic acid encoding a MUC1/X polypeptide.

21. A method of screening for a MUC1-specific antibody that binds to an intact MUC1 protein with the proviso that the antibody does not bind to either the α-subunit or the β-subunit in the absence of the other, comprising:
   i) combining a plurality of anti-MUC1 generated antibodies with a cleaved MUC1/X polypeptide;
   ii) combining a plurality of anti-MUC1 generated antibodies with a MUC1/Y polypeptide;

iii) determining the binding of the plurality of anti-MUC1 generated antibodies to the cleaved MUC1/X polypeptide and the MUC1/Y polypeptide; and
iv) selecting for antibodies that specifically bind to the MUC1/X polypeptide but do not substantially bind to the MUC1/Y polypeptide.

* * * * *

SEQUENCE LISTING

```
<160> NUMBER OF SEQ ID NOS: 15

<210> SEQ ID NO 1
<211> LENGTH: 1664
<212> TYPE: DNA
<213> ORGANISM: Homo sapiens
<220> FEATURE:
<221> NAME/KEY: misc_feature
<223> OTHER INFORMATION: mucin 1 (MUC1) isoform MUC1/TM

<400> SEQUENCE: 1
atgacaccgg gcacccagtc tcctttcttc ctgctgctgc tcctcacagt gcttacagtt      60
```

-continued

```
gttacaggtt ctggtcatgc aagctctacc ccaggtggag aaaaggagac ttcggctacc      120
cagagaagtt cagtgcccag ctctactgag aagaatgctg tgagtatgac cagcagcgta      180
ctctccagcc acagccccgg ttcaggctcc tccaccactc agggacagga tgtcactctg      240
gccccggcca cggaaccagc ttcaggttca gctgccacct ggggacagga tgtcacctcg      300
gtcccagtca ccaggccagc cctgggctcc accaccccgc agcccacga tgtcacctca      360 gccccggaca caagccagc cccgggctcc accgccccc cagcccacgg tgtcacctcg       420
gccccggaca ccaggccgcc cccgggctcc accgccccc cagcccacgg tgtcacctcg      480
gccccggaca ccaggccgcc cccgggctcc accgcgcccg cagcccacgg tgtcacctcg      540
gccccggaca ccaggccggc cccgggctcc accgccccc cagcccatgg tgtcacctcg      600
gccccggaca caggcccgc cttggcgtcc accgccctc cagtccacaa tgtcacctcg       660
gcctcaggct ctgcatcagg ctcagcttct actctggtgc acaacggcac ctctgccagg      720
gctaccacaa cccagccag caagagcact ccattctcaa ttcccagcca ccactctgat       780
actcctacca cccttgccag ccatagcacc aagactgatg ccagtagcac tcaccatagc      840
acggtacctc ctctcacctc ctccaatcac agcacttctc cccagttgtc tactggggtc      900 tcttctttt tcctgtcttt tcacatttca aacctccagt ttaattcctc tctggaagat       960
cccagcaccg actactacca agagctgcag agagacattt ctgaaatgtt tttgcagatt     1020
tataaacaag ggggttttct gggcctctcc aatattaagt tcaggccagg atctgtggtg     1080
gtacaattga ctctggcctt ccgagaaggt accatcaatg tccacgacgt ggagacacag     1140
ttcaatcagt ataaaacgga agcagcctct cgatataacc tgacgatctc agacgtcagc     1200
gtgagtgatg tgccatttcc tttctctgcc cagtctgggg ctggggtgcc aggctggggc     1260
atcgcgctgc tggtgctggt ctgtgttctg gttgcgctgg ccattgtcta tctcattgcc     1320
ttggctgtct gtcagtgccg ccgaaagaac tacgggcagc tggacatctt ccagcccgg      1380 gataccaccc atcctatgag cgagtacccc acctaccaca cccatgggcg ctatgtgccc     1440
cctagcagta ccgatcgtag ccctatgag aaggtttctg caggtaatgg tggcagcagc     1500
ctctcttaca caaacccagc agtggcagcc acttctgcca acttgtaggg gcacgtcgcc     1560
ctctgagctg agtggccagc cagtgccatt ccactccact cagggctctc tgggccagtc     1620
ctcctgggag ccccaccac aacacttccc aggcatggaa ttcc                       1664
```

<210> SEQ ID NO 2
<211> LENGTH: 515
<212> TYPE: PRT
<213> ORGANISM: Homo sapiens
<220> FEATURE:
<221> NAME/KEY: MISC_FEATURE
<223> OTHER INFORMATION: mucin 1 (MUC1) isoform MUC1/TM

<400> SEQUENCE: 2

```
Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80
```

```
Ala Pro Ala Thr Glu Pro Ala Ser Gly Ser Ala Ala Thr Trp Gly Gln
             85                  90                  95

Asp Val Thr Ser Val Pro Val Thr Arg Pro Ala Leu Gly Ser Thr Thr
                100                 105                 110

Pro Pro Ala His Asp Val Thr Ser Ala Pro Asp Asn Lys Pro Ala Pro
            115                 120                 125

Gly Ser Thr Ala Pro Pro Ala His Gly Val Thr Ser Ala Pro Asp Thr
        130                 135                 140

Arg Pro Pro Pro Gly Ser Thr Ala Pro Pro Ala His Gly Val Thr Ser
145                 150                 155                 160

Ala Pro Asp Thr Arg Pro Pro Gly Ser Thr Ala Pro Ala Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Asn Arg Pro Ala Leu
        195                 200                 205

Ala Ser Thr Ala Pro Pro Val His Asn Val Thr Ser Ala Ser Gly Ser
        210                 215                 220

Ala Ser Gly Ser Ala Ser Thr Leu Val His Asn Gly Thr Ser Ala Arg
225                 230                 235                 240

Ala Thr Thr Thr Pro Ala Ser Lys Ser Thr Pro Phe Ser Ile Pro Ser
                245                 250                 255

His His Ser Asp Thr Pro Thr Leu Ala Ser His Ser Thr Lys Thr
            260                 265                 270

Asp Ala Ser Ser Thr His His Ser Thr Val Pro Pro Leu Thr Ser Ser
        275                 280                 285

Asn His Ser Thr Ser Pro Gln Leu Ser Thr Gly Val Ser Phe Phe Phe
        290                 295                 300

Leu Ser Phe His Ile Ser Asn Leu Gln Phe Asn Ser Ser Leu Glu Asp
305                 310                 315                 320

Pro Ser Thr Asp Tyr Tyr Gln Glu Leu Gln Arg Asp Ile Ser Glu Met
                325                 330                 335

Phe Leu Gln Ile Tyr Lys Gln Gly Gly Phe Leu Gly Leu Ser Asn Ile
                340                 345                 350

Lys Phe Arg Pro Gly Ser Val Val Val Gln Leu Thr Leu Ala Phe Arg
                355                 360                 365

Glu Gly Thr Ile Asn Val His Asp Val Glu Thr Gln Phe Asn Gln Tyr
                370                 375                 380

Lys Thr Glu Ala Ala Ser Arg Tyr Asn Leu Thr Ile Ser Asp Val Ser
385                 390                 395                 400

Val Ser Asp Val Pro Phe Pro Phe Ser Ala Gln Ser Gly Ala Gly Val
                405                 410                 415

Pro Gly Trp Gly Ile Ala Leu Leu Val Leu Val Cys Val Leu Val Ala
            420                 425                 430

Leu Ala Ile Val Tyr Leu Ile Ala Leu Ala Val Cys Gln Cys Arg Arg
                435                 440                 445

Lys Asn Tyr Gly Gln Leu Asp Ile Phe Pro Ala Arg Asp Thr Tyr His
            450                 455                 460

Pro Met Ser Glu Tyr Pro Thr Tyr His Thr His Gly Arg Tyr Val Pro
465                 470                 475                 480

Pro Ser Ser Thr Asp Arg Ser Pro Tyr Glu Lys Val Ser Ala Gly Asn
                485                 490                 495

Gly Gly Ser Ser Leu Ser Tyr Thr Asn Pro Ala Val Ala Ala Thr Ser
            500                 505                 510
```

Ala Asn Leu
    515

<210> SEQ ID NO 3
<211> LENGTH: 1209
<212> TYPE: DNA
<213> ORGANISM: Homo sapiens
<220> FEATURE:
<221> NAME/KEY: misc_feature
<223> OTHER INFORMATION: mucin 1 (MUC1) isoform MUC1/X

<400> SEQUENCE: 3

```
acctctcaag cagccagcgc ctgcctgaat ctgttctgcc ccctccccac ccatttcacc    60
accaccatga caccgggcac ccagtctcct ttcttcctgc tgctgctcct cacagtgctt   120
acagttgtta cgggttctgg tcatgcaagc tctaccccag gtggagaaaa ggagacttcg   180
gctacccaga gaagttcagt gcccagctct actgagaaga atgctttgtc tactggggtc   240
tctttctttt tcctgtcttt tcacatttca aacctccagt ttaattcctc tctggaagat   300
cccagcaccg actactacca agagctgcag agagacattt ctgaaatgtt tttgcagatt   360
tataaacaag gggttttctc tggcctctcc aatattaagt tcaggccagg atctgtggtg   420
gtacaattga ctctggcctt ccgagaaggt accatcaatg tccacgacgt ggagacacag   480
ttcaatcagt ataaaacgga agcagcctct cgatataacc tgacgatctc agacgtcagc   540
gtgagtgatg tgccatttcc tttctctgcc cagtctgggg ctggggtgcc aggctgggc    600
atcgcgctgc tggtgctggt ctgtgttctg gttgcgctgg ccattgtcta tctcattgcc   660
ttggctgtct gtcagtgccg ccgaaagaac tacgggcagc tggacatctt ccagcccgg    720
gatacctacc atcctatgag cgagtacccc acctaccaca ccatgggcg ctatgtgccc    780
cctagcagta ccgatcgtag cccctatgag aaggtttctg caggtaatgg tggcagcagc   840
ctctcttaca caaacccagc agtggcagcc acttctgcca acttgtaggg gcacgtcgcc   900
cgctgagctg agtggccagc cagtgccatt ccactccact caggttcttc agggccagag   960
cccctgcacc ctgtttgggc tggtgagctg ggagttcagg tgggctgctc acagcctcct  1020
tcagaggccc caccaatttc tcggacactt ctcagtgtgt ggaagctcat gtgggcccct  1080
gagggctcat gcctgggaag tgttgtggtg ggggctccca ggaggactgg cccagagagc  1140
cctgagatag cggggatcct gaactggact gaataaaacg tggtctccca ctgcgccaaa  1200
aaaaaaaaa                                                          1209
```

<210> SEQ ID NO 4
<211> LENGTH: 273
<212> TYPE: PRT
<213> ORGANISM: Homo sapiens
<220> FEATURE:
<221> NAME/KEY: MISC_FEATURE
<223> OTHER INFORMATION: mucin 1 (MUC1) isoform MUC1/X

<400> SEQUENCE: 4

Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Leu Ser Thr Gly Val Ser Phe Phe Phe Leu Ser
    50                  55                  60

```
Phe His Ile Ser Asn Leu Gln Phe Asn Ser Ser Leu Glu Asp Pro Ser
 65                  70                  75                  80

Thr Asp Tyr Tyr Gln Glu Leu Gln Arg Asp Ile Ser Glu Met Phe Leu
             85                  90                  95

Gln Ile Tyr Lys Gln Gly Gly Phe Leu Gly Leu Ser Asn Ile Lys Phe
            100                 105                 110

Arg Pro Gly Ser Val Val Val Gln Leu Thr Leu Ala Phe Arg Glu Gly
        115                 120                 125

Thr Ile Asn Val His Asp Val Glu Thr Gln Phe Asn Gln Tyr Lys Thr
    130                 135                 140

Glu Ala Ala Ser Arg Tyr Asn Leu Thr Ile Ser Asp Val Ser Val Ser
145                 150                 155                 160

Asp Val Pro Phe Pro Phe Ser Ala Gln Ser Gly Ala Gly Val Pro Gly
                165                 170                 175

Trp Gly Ile Ala Leu Leu Val Leu Val Cys Val Leu Val Ala Leu Ala
            180                 185                 190

Ile Val Tyr Leu Ile Ala Leu Ala Val Cys Gln Cys Arg Arg Lys Asn
        195                 200                 205

Tyr Gly Gln Leu Asp Ile Phe Pro Ala Arg Asp Thr Tyr His Pro Met
    210                 215                 220

Ser Glu Tyr Pro Thr Tyr His Thr His Gly Arg Tyr Val Pro Pro Ser
225                 230                 235                 240

Ser Thr Asp Arg Ser Pro Tyr Glu Lys Val Ser Ala Gly Asn Gly Gly
                245                 250                 255

Ser Ser Leu Ser Tyr Thr Asn Pro Ala Val Ala Ala Thr Ser Ala Asn
            260                 265                 270

Leu

<210> SEQ ID NO 5
<211> LENGTH: 1155
<212> TYPE: DNA
<213> ORGANISM: Homo sapiens
<220> FEATURE:
<221> NAME/KEY: misc_feature
<223> OTHER INFORMATION: mucin 1 (MUC1) isoform MUC1/Y

<400> SEQUENCE: 5
acctctcaag cagccagcgc ctgcctgaat ctgttctgcc cctcccccac ccatttcacc      60
accaccatga caccgggcac ccagtctcct ttcttcctgc tgctgctcct cacagtgctt     120
acagttgtta cggttctggg tcatgcaagc tctaccccag gtggagaaaa ggagacttcg     180
gctacccaga gaagttcagt gcccagctct actgagaaga atgcttttaa ttcctctctg     240
gaagatccca gcaccgacta ctaccaagag ctgcagagag acatttctga atgttttttg     300
cagatttata acaaggggg ttttctgggc ctctccaata ttaagttcag gccaggatct     360
gtggtggtac aattgactct ggccttccga gaaggtacca tcaatgtcca cgacgtggag     420
acacagttca atcagtataa aacggaagca gcctctcgat ataacctgac gatctcagac     480
gtcagcgtga gtgatgtgcc atttcctttc tctgcccagt ctggggctgg ggtgccaggc     540
tggggcatcg cgctgctggt gctggtctgt gttctggttg cgctggccat tgtctatctc     600
attgccttgg ctgtctgtca gtgccgccga aagaactacg ggcagctgga catctttcca     660
gcccgggata cctaccatcc tatgagcgag taccccacct accacaccca tgggcgctat     720 gtgccccta gcagtaccga tcgtagcccc tatgagaagg tttctgcagg taatggtggc     780
agcagcctct cttacacaaa cccagcagtg gcagccactt ctgccaactt gtaggggcac     840
```

-continued

```
gtcgcccgct gagctgagtg gccagccagt gccattccac tccactcagg ttcttcaggg      900
ccagagcccc tgcaccctgt ttgggctggt gagctgggag ttcaggtggg ctgctcacag      960
cctccttcag aggccccacc aatttctcgg acacttctca gtgtgtggaa gctcatgtgg     1020
gcccctgagg gctcatgcct gggaagtgtt gtggtggggg ctcccaggag gactggccca     1080
gagagccctg agatagcggg gatcctgaac tggactgaat aaaacgtggt ctcccactgc     1140
gccaaaaaaa aaaaa                                                       1155
```

<210> SEQ ID NO 6
<211> LENGTH: 255
<212> TYPE: PRT
<213> ORGANISM: Homo sapiens
<220> FEATURE:
<221> NAME/KEY: MISC_FEATURE
<223> OTHER INFORMATION: mucin 1 (MUC1) isoform MUC1/Y

<400> SEQUENCE: 6

```
Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Phe Asn Ser Ser Leu Glu Asp Pro Ser Thr Asp
    50                  55                  60

Tyr Tyr Gln Glu Leu Gln Arg Asp Ile Ser Glu Met Phe Leu Gln Ile
65                  70                  75                  80

Tyr Lys Gln Gly Gly Phe Leu Gly Leu Ser Asn Ile Lys Phe Arg Pro
                85                  90                  95

Gly Ser Val Val Val Gln Leu Thr Leu Ala Phe Arg Glu Gly Thr Ile
            100                 105                 110

Asn Val His Asp Val Glu Thr Gln Phe Asn Gln Tyr Lys Thr Glu Ala
        115                 120                 125

Ala Ser Arg Tyr Asn Leu Thr Ile Ser Asp Val Ser Val Ser Asp Val
    130                 135                 140

Pro Phe Pro Phe Ser Ala Gln Ser Gly Ala Gly Val Pro Gly Trp Gly
145                 150                 155                 160

Ile Ala Leu Leu Val Leu Val Cys Val Leu Val Ala Leu Ala Ile Val
                165                 170                 175

Tyr Leu Ile Ala Leu Ala Val Cys Gln Cys Arg Arg Lys Asn Tyr Gly
            180                 185                 190

Gln Leu Asp Ile Phe Pro Ala Arg Asp Thr Tyr His Pro Met Ser Glu
        195                 200                 205

Tyr Pro Thr Tyr His Thr His Gly Arg Tyr Val Pro Pro Ser Ser Thr
    210                 215                 220

Asp Arg Ser Pro Tyr Glu Lys Val Ser Ala Gly Asn Gly Gly Ser Ser
225                 230                 235                 240

Leu Ser Tyr Thr Asn Pro Ala Val Ala Ala Thr Ser Ala Asn Leu
                245                 250                 255
```

<210> SEQ ID NO 7
<211> LENGTH: 1721
<212> TYPE: DNA
<213> ORGANISM: Homo sapiens
<220> FEATURE:
<221> NAME/KEY: misc_feature
<223> OTHER INFORMATION: mucin 1 (MUC1), MUC1/TM, MUC1/X and MUC1/Y
    isoforms

<400> SEQUENCE: 7

```
gaattccctg gctgcttgaa tctgttctgc ccctccccca cccatttcac caccaccatg    60
acaccgggca cccagtctcc tttcttcctg ctgctgctcc tcacagtgct tacagttgtt   120
acaggttctg gtcatgcaag ctctacccca ggtggagaaa aggagacttc ggctacccag   180
agaagttcag tgcccagctc tactgagaag aatgctgtga gtatgaccag cagcgtactc   240
tccagccaca gccccggttc aggctcctcc accactcagg acaggatgt cactctggcc    300
ccggccacgg aaccagcttc aggttcagct gccacctggg acaggatgt cacctcggtc    360
ccagtcacca ggccagccct gggctccacc accccgccag cccacgatgt cacctcagcc   420
ccggacaaca gccagccccc gggctccacc gccccccag cccacggtgt cacctcggcc    480
ccggacacca ggccgccccc gggctccacc gccccccag cccacggtgt cacctcggcc    540
ccggacacca ggccgccccc gggctccacc gcgccgcag cccacggtgt cacctcggcc    600
ccggacacca ggccggcccc gggctccacc gcccccag cccatggtgt cacctcggcc     660
ccggacaaca ggcccgcctt ggcgtccacc gcccctccag tccacaatgt cacctcggcc   720
tcaggctctg catcaggctc agcttctact ctggtgcaca acggcacctc tgccagggct   780
accacaaccc cagccagcaa gagcactcca ttctcaattc ccagccacca ctctgatact   840
cctaccaccc ttgccagcca tagcaccaag actgatgcca gtagcactca ccatagcacg   900
gtacctcctc tcacctcctc caatcacagc acttctcccc agttgtctac tggggtctct   960
ttcttttttcc tgtcttttca catttcaaac ctccagttta attcctctct ggaagatccc 1020
agcaccgact actaccaaga gctgcagaga gacatttctg aaatgttttt gcagatttat 1080
aaacaagggg gttttctggg cctctccaat attaagttca ggccaggatc tgtggtggta 1140
caattgactc tggccttccg agaaggtacc atcaatgtcc acgacgtgga gacacagttc 1200
aatcagtata aaacggaagc agcctctcga tataacctga cgatctcaga cgtcagcgtg 1260
agtgatgtgc catttccttt ctctgcccag tctggggctg gggtgccagg ctggggcatc 1320
gcgctgctgg tgctggtctg tgttctggtt gcgctggcca ttgtctatct cattgccttg 1380
gctgtctgtc agtgccgccg aaagaactac gggcagctgg acatctttcc agcccgggat 1440
acctaccatc ctatgagcga gtaccccacc taccacaccc atgggcgcta tgtgcccccct 1500
agcagtaccg atcgtagccc ctatgagaag gtttctgcag gtaatggtgg cagcagcctc 1560
tcttacacaa acccagcagt ggcagccact tctgccaact tgtagggca cgtcgccctc  1620
tgagctgagt ggccagccag tgccattcca ctccactcag ggctctctgg gccagtcctc 1680
ctgggagccc ccaccacaac acttcccagg catggaattc                       1721
```

<210> SEQ ID NO 8
<211> LENGTH: 30
<212> TYPE: PRT
<213> ORGANISM: Homo sapiens
<220> FEATURE:
<221> NAME/KEY: MISC_FEATURE
<223> OTHER INFORMATION: N30 sequence

<400> SEQUENCE: 8

```
Ser Gly His Ala Ser Ser Thr Pro Gly Gly Glu Lys Glu Thr Ser Ala
1               5                   10                  15
Thr Gln Arg Ser Ser Val Pro Ser Ser Thr Glu Lys Asn Ala
            20                  25                  30
```

<210> SEQ ID NO 9

```
<211> LENGTH: 5
<212> TYPE: PRT
<213> ORGANISM: Artificial Sequence
<220> FEATURE:
<223> OTHER INFORMATION: N-terminus of N30 sequence

<400> SEQUENCE: 9

Ser Gly His Ala Ser
1               5

<210> SEQ ID NO 10
<211> LENGTH: 4
<212> TYPE: PRT
<213> ORGANISM: Artificial Sequence
<220> FEATURE:
<223> OTHER INFORMATION: C-terminus of N30 sequence

<400> SEQUENCE: 10

Glu Lys Asn Ala
1

<210> SEQ ID NO 11
<211> LENGTH: 120
<212> TYPE: PRT
<213> ORGANISM: Artificial Sequence
<220> FEATURE:
<223> OTHER INFORMATION: MUC1/X amino acids immediately C-terminal to
      the MUC1/X splice acceptor site, N-terminal to transmembrane
      domain

<400> SEQUENCE: 11

Leu Ser Thr Gly Val Ser Phe Phe Leu Ser Phe His Ile Ser Asn
1               5                   10                  15

Leu Gln Phe Asn Ser Ser Leu Glu Asp Pro Ser Thr Asp Tyr Tyr Gln
            20                  25                  30

Glu Leu Gln Arg Asp Ile Ser Glu Met Phe Leu Gln Ile Tyr Lys Gln
        35                  40                  45

Gly Gly Phe Leu Gly Leu Ser Asn Ile Lys Phe Arg Pro Gly Ser Val
    50                  55                  60

Val Val Gln Leu Thr Leu Ala Phe Arg Glu Gly Thr Ile Asn Val His
65                  70                  75                  80

Asp Val Glu Thr Gln Phe Asn Gln Tyr Lys Thr Glu Ala Ala Ser Arg
                85                  90                  95

Tyr Asn Leu Thr Ile Ser Asp Val Ser Val Ser Asp Val Pro Phe Pro
            100                 105                 110

Phe Ser Ala Gln Ser Gly Ala Gly
        115                 120

<210> SEQ ID NO 12
<211> LENGTH: 4
<212> TYPE: PRT
<213> ORGANISM: Artificial Sequence
<220> FEATURE:
<223> OTHER INFORMATION: N-terminus of MUC1/X amino acids immediately C-
      terminal to the MUC1/X splice acceptor site, N-terminal to
      transmembrane domain

<400> SEQUENCE: 12

Leu Ser Thr Gly
1

<210> SEQ ID NO 13
<211> LENGTH: 4
<212> TYPE: PRT
<213> ORGANISM: Artificial Sequence
```

```
<220> FEATURE:
<223> OTHER INFORMATION: C-terminus of MUC1/X amino acids immediately C-
      terminal to the MUC1/X splice acceptor site, N-terminal to
      transmembrane domain

<400> SEQUENCE: 13

Ser Gly Ala Gly
1

<210> SEQ ID NO 14
<211> LENGTH: 5
<212> TYPE: PRT
<213> ORGANISM: Artificial Sequence
<220> FEATURE:
<223> OTHER INFORMATION: amino acids at cleavage site of MUC1/TM between
      Gly 357 and Ser 358, between MUC1/X amino acids 62 and 63

<400> SEQUENCE: 14

Gly Ser Val Val Val
1               5

<210> SEQ ID NO 15
<211> LENGTH: 8
<212> TYPE: PRT
<213> ORGANISM: Artificial Sequence
<220> FEATURE:
<223> OTHER INFORMATION: FLAG purification and/or detection tag

<400> SEQUENCE: 15

Asp Tyr Lys Asp Asp Asp Asp Lys
1               5
```